US010898316B2

(12) United States Patent
Ellis

(10) Patent No.: US 10,898,316 B2
(45) Date of Patent: Jan. 26, 2021

(54) INTRAOCULAR LENS

(71) Applicant: Forrest J. Ellis, McLean, VA (US)

(72) Inventor: Forrest J. Ellis, McLean, VA (US)

(73) Assignee: JELLISEE OPHTHALMICS INC, McLean, VA (US)

(*) Notice: Subject to any disclaimer, the term of this patent is extended or adjusted under 35 U.S.C. 154(b) by 65 days.

(21) Appl. No.: 16/288,723

(22) Filed: Feb. 28, 2019

(65) Prior Publication Data
US 2019/0269499 A1 Sep. 5, 2019

Related U.S. Application Data

(60) Provisional application No. 62/636,971, filed on Mar. 1, 2018, provisional application No. 62/746,603, filed on Oct. 17, 2018.

(51) Int. Cl.
A61F 2/16 (2006.01)
A61F 9/007 (2006.01)

(52) U.S. Cl.
CPC ........ A61F 2/1613 (2013.01); A61F 2/16015 (2015.04); A61F 2/1694 (2013.01); A61F 9/00736 (2013.01); A61F 2/1624 (2013.01); A61F 2/1635 (2013.01); A61F 2/1648 (2013.01); A61F 2002/1681 (2013.01); A61F 2002/1682 (2015.04); A61F 2002/16901 (2015.04); A61F 2002/16902 (2015.04); A61F 2250/0003 (2013.01); A61L 2430/16 (2013.01)

(58) Field of Classification Search
CPC .................. A61F 2/1624; A61F 2/1635; A61F 2002/1682; A61F 2002/1681; A61F 2/1648; A61F 2002/16902; A61F 2/1694; A61F 2/1613
See application file for complete search history.

(56) References Cited

U.S. PATENT DOCUMENTS

| 6,551,354 | B1 | 4/2003 | Ghazizadeh et al. |
| 7,025,783 | B2 | 4/2006 | Brady et al. |
| 7,097,660 | B2 | 8/2006 | Portney |
| 7,326,246 | B2 | 2/2008 | Brady et al. |
| 8,109,998 | B2 | 2/2012 | Cumming |
| 8,858,626 | B2 | 10/2014 | Noy |
| 9,107,748 | B2 | 8/2015 | De Juan, Jr. et al. |
| 9,433,498 | B2 | 9/2016 | Masket |

(Continued)

FOREIGN PATENT DOCUMENTS

WO 2015/153291 A1 10/2015

OTHER PUBLICATIONS

PCT International Search Report and Written Opinion for corresponding Application No. PCT/US2019/019972, dated Jul. 29, 2019, pp. 1-20.

Primary Examiner — David H Willse
Assistant Examiner — Javier G Blanco
(74) Attorney, Agent, or Firm — Tarolli, Sundheim, Covell & Tummino LLP

(57) ABSTRACT

An accommodating intraocular lens (IOL) is provided. The IOL includes an optic having an anterior face and a posterior face. One or more centration lips are disposed directly on the posterior and/or anterior face of the optic or directly on the posterior and/or anterior face of a carrier that holds the optic. Anterior centration lips are configured to center the optic in a lens capsulotomy opening. Posterior centration lips are configured to fixate the optic in a lens capsule and also center the optic in a lens capsulotomy opening.

7 Claims, 25 Drawing Sheets

(56) References Cited

U.S. PATENT DOCUMENTS

| | | |
|---|---|---|
| 9,504,560 B2 | 11/2016 | Brady et al. |
| 9,554,893 B2 | 1/2017 | Brady et al. |
| 9,603,703 B2 | 3/2017 | Bumbalough |
| 9,629,712 B2 | 4/2017 | Stenger |
| 9,636,213 B2 | 5/2017 | Brady |
| 9,717,589 B2 | 8/2017 | Simonov et al. |
| 9,744,028 B2 | 8/2017 | Simonov et al. |
| 9,814,568 B2 | 11/2017 | Ben Nun |
| 9,872,762 B2 | 1/2018 | Scholl et al. |
| 9,913,712 B2 | 3/2018 | Reich et al. |
| 9,968,442 B2 | 5/2018 | Akura |
| 9,987,125 B2 | 6/2018 | Brady et al. |
| 10,004,595 B2 | 6/2018 | Liu et al. |
| 10,004,596 B2 | 6/2018 | Brady et al. |
| 10,028,823 B2 | 7/2018 | Akura |
| 10,052,194 B2 | 8/2018 | Bumbalough |
| 10,105,215 B2 | 10/2018 | Bumbalough |
| 10,111,745 B2 | 10/2018 | Silvestrini et al. |
| 10,159,564 B2 | 12/2018 | Brady et al. |
| 10,166,096 B2 | 1/2019 | Ben Nun |
| 10,195,018 B2 | 2/2019 | Salahieh et al. |
| 10,206,773 B2 | 2/2019 | Paul et al. |
| 10,219,893 B2 | 3/2019 | Currie et al. |
| 2010/0106245 A1 | 4/2010 | Rombach et al. |
| 2011/0153015 A1 | 6/2011 | Simonov et al. |
| 2015/0173891 A1 | 6/2015 | Devita Gerardi et al. |
| 2015/0173892 A1 | 6/2015 | Borja et al. |
| 2016/0128826 A1 | 5/2016 | Silvestrini et al. |
| 2016/0184089 A1 | 6/2016 | Dudee et al. |
| 2016/0317286 A1 | 11/2016 | Brady et al. |
| 2016/0317287 A1 | 11/2016 | Silvestrini et al. |
| 2016/0331520 A1 | 11/2016 | Beer |
| 2017/0020662 A1 | 1/2017 | Shadduck |
| 2017/0065405 A1 | 3/2017 | Brady et al. |
| 2017/0172732 A1 | 6/2017 | Liu et al. |
| 2017/0181850 A1 | 6/2017 | De Juan, Jr. et al. |
| 2017/0216021 A1 | 8/2017 | Brady |
| 2017/0258580 A1 | 9/2017 | Bumbalough |
| 2017/0281334 A1 | 10/2017 | Zhao |
| 2017/0319332 A1 | 11/2017 | Kahook et al. |
| 2018/0055626 A1 | 3/2018 | Beer |
| 2018/0104047 A1 | 4/2018 | Callahan |
| 2018/0125640 A1 | 5/2018 | Smiley et al. |
| 2018/0147051 A1 | 5/2018 | Scholl et al. |
| 2018/0161152 A1 | 6/2018 | Argento et al. |
| 2018/0177589 A1 | 6/2018 | Argento et al. |
| 2018/0177693 A1 | 6/2018 | Shimokawa et al. |
| 2018/0256315 A1 | 9/2018 | Hildebrand et al. |
| 2018/0318066 A1 | 11/2018 | Campin et al. |
| 2018/0353288 A1 | 12/2018 | Bumbalough |
| 2019/0000612 A1 | 1/2019 | Rao et al. |
| 2019/0038401 A1 | 2/2019 | Reich et al. |
| 2019/0053893 A1 | 2/2019 | Currie et al. |
| 2019/0099263 A1 | 4/2019 | Brady et al. |

INTRAOCULAR LENS

CROSS-REFERENCE TO RELATED APPLICATIONS

The present application claims priority to U.S. Provisional Application No. 62/746,603, filed on Oct. 17, 2018 and U.S. Provisional Application No. 62/636,971, filed on Mar. 1, 2018. The contents of both applications are incorporated by reference in their entirety.

TECHNICAL FIELD

The present disclosure relates to an intraocular lens system.

BACKGROUND

With aging, the lens of the human eye becomes more rigid and this results in a reduction in the ability to change focus from distance to near (presbyopia). Also, with aging, the lens of the eye becomes optically less clear (a cataract), resulting in reduced visual clarity. Removal of the cataract lens and replacement with an artificial intraocular lens (IOL) is performed when the cataract sufficiently reduces visual acuity and/or visual quality. Monofocal intraocular lenses are standard and widely utilized as a replacement when the natural lens (cataract) of the eye is removed. These lenses allow for a single point of best focus. None of the monofocal lenses change dioptric power with near focus and most patients elect to wear spectacle lenses (e.g. glasses) to achieve focus at varying distances. Accommodation is the increase in the dioptric power of the natural lens of the eye with near focus. This occurs by contraction of the ciliary muscle of the eye with resultant reduction in tension on the lens suspensory fibers (lens zonules). This reduction in tension on the zonules allows the elastic natural lens of the eye to increase in curvature and results in increased dioptric power of the lens, facilitating focus at near. The development of a suitable artificial IOL for placement after removal of the natural lens of the eye (e.g. cataract removal or clear lens extraction) capable of a sufficient level of accommodation (e.g. an increase in dioptric power for focus at near in response to ciliary muscle contraction) remains a challenge.

There are generally two classes of IOLs that have been developed that attempt to overcome the lack of accommodation of an IOL used to replace the natural lens when cataract surgery is performed: pseudo-accommodating lenses and accommodating lenses. Pseudo-accommodating lenses are either a multiple focal point lens, which use a ring for distance focus and a center optic for near focus, or use diffraction optics to obtain a range of focus or use optics to achieve an extended depth of focus (EDF). Multi-focus optics, diffraction optics, and EDF optic designs result in disruptive optical aberrations such as glare, halos, reduced contrast sensitivity, etc. Centration of these lenses within the capsular bag is important to their best visual function. These lenses use non-deforming optical elements and do not achieve the visual quality of a natural, youthful lens of the human eye. The accommodating class of IOLs includes a silicone elastomeric hinged lens that allows forward movement of the optic when the eye focuses at near. These lenses are typically placed in the lens capsular bag (the remaining thin layer of basement membrane that is the outermost layer of the natural lens and is typically left in place when the contents of the lens are removed during cataract surgery). Due to progressive fibrosis and stiffening of the lens capsule following cataract removal, the effective accommodation with these lenses is known to diminish over time. Overall, these lenses are adequate for distance and intermediate vision, but only provide accommodation of about two diopters at most and this value has been shown to diminish over time.

To function like a natural youthful human eye, a replacement lens would, in response to gradual contraction of the ciliary muscle of the eye, gradually increase in overall dioptric power of sufficient magnitude to allow a range of focus similar to a more youthful natural lens of the eye. The above-described lenses do not have these properties. Such properties would allow a lens to change optical power with attempted near focus without inducing irregular astigmatism or other significant optical aberrations.

SUMMARY

In an aspect, the present disclosure provides an intraocular lens (IOL) comprising an optic having an anterior face, a posterior face, a right side, a left side, an optical axis extending in an anterior-posterior direction, and an equator extending in a plane substantially perpendicular to the optical axis. The IOL includes a right haptic having a lateral portion with a lateral end and a medial portion with a medial end. The medial end is in communication with the right side of the optic. The IOL also includes a left haptic having a lateral portion with a lateral end and a medial portion with a medial end. The medial end is in communication with the left side of the optic. The IOL also includes one or more centration lips disposed directly or indirectly on the posterior face and/or the anterior face of the optic. The one or more centration lips are configured to center the optic in a lens capsulotomy opening.

In another aspect, the present disclosure provides an IOL comprising a deformable optic having an anterior face, a posterior face, an optical axis extending in an anterior-posterior direction, and an equator extending in a plane substantially perpendicular to the optical axis. A sleeve is disposed about the equator of the optic and defines a lumen. The sleeve comprises a first sleeve segment and a second sleeve segment. The IOL also includes a translating arm disposed about the equator of the deformable optic opposite the sleeve. The translating arm comprises a first translating arm segment glidably received by the first sleeve segment and a second translating arm segment glidably received by the second sleeve segment. The IOL also includes a right haptic having a medial portion with a medial end and a lateral portion with a lateral end, the medial end coupled to the sleeve. Similarly, the IOL includes a left haptic having a medial portion with a medial end and a lateral portion with a lateral end, the medial end coupled to the translating arm.

In another aspect, the present disclosure provides an IOL comprising an optic having an optical axis extending in an anterior-posterior direction, a posterior face, an anterior face, and an equator extending in a plane substantially perpendicular to the optical axis. A substantially rigid ring having a right side, a left side, and defining an interior chamber is disposed about the equator of the optic. The interior chamber comprises a first portion housing a first plurality of circumferentially spaced springs connected by a first filament having a right end and a left end and a second portion housing a second plurality of circumferentially spaced springs connected by a second filament having a right end and a left end. A right haptic is in communication with the right side of the substantially rigid ring and the right ends of the first filament and the second filament are directly or indirectly connected to the right haptic. A left haptic is in communication with the left side of the substantially rigid ring and the left ends of the first filament and the second filament directly or indirectly connected to the right haptic.

In another aspect, the present disclosure provides an IOL comprising an optic having an optical axis extending in an anterior-posterior direction, a posterior face, an anterior face, and an equator extending in a plane substantially perpendicular to the optical axis. The IOL further comprises a compressible capsule having a right side and a left side and disposed about the equator of the optic. The IOL also include a right haptic having a lateral portion with a lateral end and a medial portion with a medial end. The medial end of the right haptic is in communication with the right side of the compressible capsule. Similarly, the IOL also includes a left haptic having a lateral portion with a lateral end and a medial portion with a medial end. The medial end of the left haptic is in communication with the left side of the compressible capsule.

In another aspect, the present disclosure provides an IOL comprising an optic having an optical axis extending in an anterior-posterior direction, a posterior face, an anterior face, a right side, a left side, and an equator extending in a plane substantially perpendicular to the optical axis. The IOL also includes a substantially J-shaped right haptic in communication with the right side of the optic, the substantially J-shaped right haptic having a lateral portion with a lateral end and a medial portion with a medial end. The lateral end of the substantially J-shaped right haptic curves posteriorly towards the medial end of the right haptic. Similarly, the IOL includes a substantially J-shaped left haptic in communication with the left side of the optic, the substantially J-shaped left haptic having a lateral portion with a lateral end and a medial portion with a medial end. The lateral end of the substantially J-shaped left haptic curves posteriorly towards the medial end of the left haptic.

In another aspect, the present disclosure provides an IOL comprising an optic having an optical axis extending in an anterior-posterior direction, a posterior face, an anterior face, a right side, a left side, and an equator extending in a plane substantially perpendicular to the optical axis. The IOL also includes a right haptic in communication with the right side of the optic, the right haptic having a lateral portion with a lateral end and a medial portion with a medial end. The lateral portion of the right haptic are ridges are the leading edge of the lateral portion of the right haptic is smoother and narrower than the trailing edge of the lateral end of the right haptic. Similarly, the IOL includes a left haptic in communication with the left side of the optic, the left haptic having a lateral portion with a lateral end and a medial portion with a medial end. The lateral portion of the left haptic are ridges are the leading edge of the lateral portion of the left haptic is smoother and narrower than the trailing edge of the lateral end of the left haptic.

The present disclosure also provides for IOLs combining one or more of the above-described aspects.

BRIEF DESCRIPTION OF DRAWINGS

The following drawings are schematic in nature and are not necessarily to scale both in terms of specific components and components as they relate to one another. Rather, certain components are enlarged for purposes of clarity.

DETAILED DESCRIPTION

Figure 1:
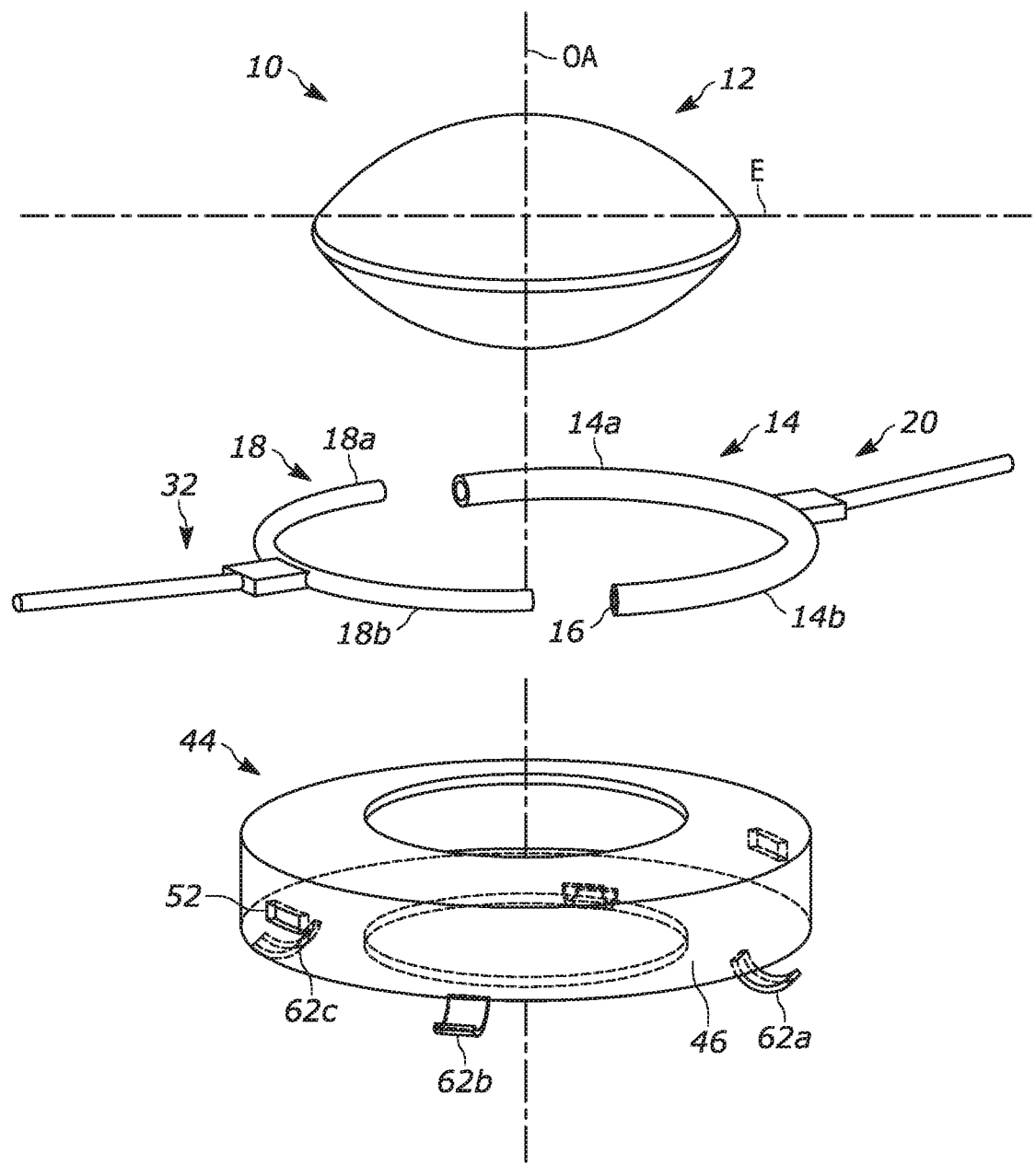
FIG. 1 is an exploded view of an embodiment of an IOL according to an aspect of the present disclosure.

The present disclosure relates to an intraocular lens (IOL) such as, for example, an accommodative IOL. As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. By "substantially" is meant that the direction, shape, or configuration of described element need not have the mathematically exact described direction, shape, or configuration of the described element or term but can have a direction, shape, or configuration that is recognizable by one skilled in the art as generally or approximately having the described direction, shape, or configuration of the described element. As used herein, the terms "anterior," "posterior," "front," "back," "lateral," and "medial" refer to the position of elements when a patient is in a standard anatomical position. The terms "left" and "right" refer to the position of elements as they are depicted in the drawings and the terms "left" and "right" can be interchanged unless indicated otherwise. The terms "first," "second," etc. are only used to distinguish one element from another unless indicated otherwise. Thus, a "first" element described below could also be termed a "second" element. The sequence of operations (or steps) is not limited to the order presented in the claims or figures unless specifically indicated otherwise. By "integral" or "integrated" is meant that the described components are fabricated as one piece during manufacturing or the described components are otherwise not separable using a normal amount of force without damaging the integrity (i.e. tearing) of either of the components. A normal amount of force is the amount of force a user would use to remove a component meant to be separated from another component without damaging either component. A "deformable" optic" as used herein is an optic fabricated from a material that allows the optic to change shape in accommodative and non-accommodative states. In other words, the optic is deformable such that the inward pressure or outward tension on the optic caused by ciliary muscle contraction or relaxation causes the optic to change shape. As used herein a "patient" includes a mammal such as a human being. All IOLs as described herein are used for medical purposes and are therefore sterile. Components of IOLs as described herein can be used with IOLs described herein as well as other IOLs including an IOL placed anterior to an existing, previously placed IOL. IOLs include fixed power, multifocal, EDF, diffractive and other variable focus lenses. Although the drawings show certain elements of an IOL in combination, it should be noted that such elements can be included in other embodiments illustrated in other drawings. In other words, each of the disclosed aspects and embodiments of the present disclosure may be considered individually or in combination with other aspects and embodiments of the disclosure.

Referring to FIGS. 1-5, in an aspect, an IOL 10 can include optic 12 having optical axis OA extending in an anterior-posterior direction and having equator E extending in a plane substantially perpendicular to optical axis OA. The optic can be fabricated, for example, from a semi-solid material such as silicone, acrylic (hydrophilic or hydrophobic), or other types of malleable optical material compound, or comprise an optical fluid contained within an elastic or malleable membrane. In certain embodiments, the optic is a deformable optic.

Figure 5:
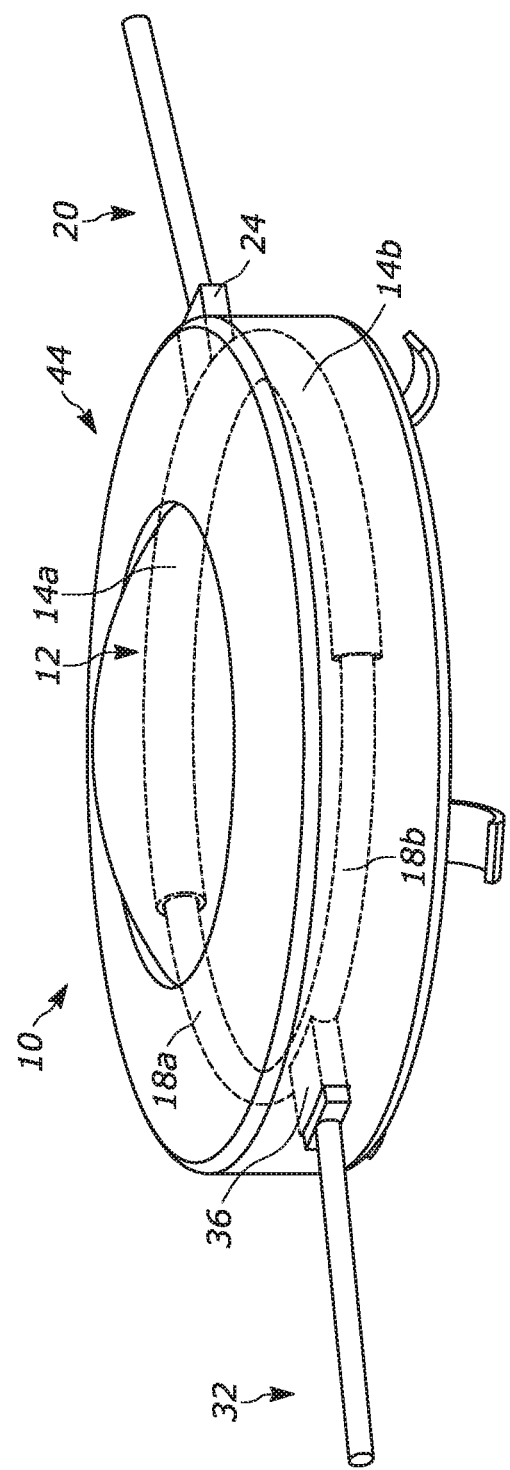
FIG. 5 is perspective view of an embodiment of an IOL according to an aspect of the present disclosure.

IOL 10 can further include sleeve 14 disposed about equator E of optic 12 and defining lumen 16. Sleeve 14 can comprise first sleeve segment 14a and second sleeve segment 14b. Translating arm 18 can be disposed about equator E of optic 12 opposite sleeve 14. Translating arm 18 can comprise first translating arm segment 18a glidably receivable by first sleeve segment 14a and second translating arm segment 18b glidably receivable by second sleeve segment 14b as illustrated in FIG. 5. The sleeve and translating arms interact with one another to increase the dioptric power of the optic when the ciliary muscle contracts and the optic assumes an accommodated state. As described above, the ciliary muscle controls the curvature of the lens and changes the shape of the lens when the patient's eye focuses on a near object. In other words, when the ciliary muscle contracts, the translating arm and the sleeve come together medially with the segments of the translating arm gliding in a medial direction deeper in the lumens of the respective sleeve segments. This results in reduction of the equatorial diameter of the optic and increases the curvature of the anterior and posterior faces of the optic. The translating arm and sleeve can be fabricated from a semi-rigid material. By having semi-rigid translating arms, the peripheral tension can remain substantially equal in all areas of the optic, reducing or eliminating the need for diffractive optics, multifocal optics or extended depth of focus optics. An elastic membrane can surround the sleeve and translating arms to avoid fibrosis and restriction of the moveable elements of an IOL. In other words, the moveable parts of an IOL can be sealed to allow for free movement, thus isolating the moveable parts from ocular fluid to avoid inflammatory cells and other substances from interfering with the function of the moveable parts.

IOL 10 can also comprise right haptic 20 having medial portion 22 with medial end 24 and lateral portion 26 with lateral end 28. Medial end 24 can be coupled to sleeve 14. Likewise, IOL 10 can include left haptic 32 having medial portion 34 with medial end 36 and a lateral portion 38 with lateral end 40. Medial end 36 can be coupled to translating arm 18. It is understood that the terms "right" and "left" are only used to identify the haptics and the right haptic could be interchanged with the left haptic such that the right haptic is coupled to the translating arm and the left haptic is coupled to the sleeve. When the ciliary muscle contracts, the haptics transfer the pressure from the ciliary muscle to the translating arm and the sleeve, causing the translating arm to glide within the lumen of the sleeve and the sleeve to glide over the translating arm and thereby constricting the equatorial diameter of the optic. The haptics can be fabricated from a semi-rigid material.

Figure 4:
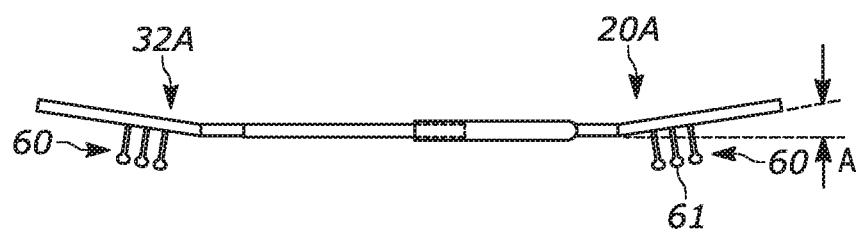
FIG. 4 is a side view of an embodiment of a translating arm, a sleeve, a right haptic, and a left haptic of an IOL according to an aspect of the present disclosure.

Referring to FIG. 4, in an embodiment, right haptic and left haptic 20A and 32A can include one or more stabilizing members 60 disposed on a posterior surface thereof. Such stabilizing members can interdigitate with the zonules to stabilize the optic. As stated above, zonules are the fibrous strands that connect the ciliary muscle with a crystalline lens of a patient's eye and hold the eye in place. The stabilizing members can be in the shape of a knob, for example, with blunt distal end 61 to avoid damage or tearing of the zonules. With haptic interaction with the ciliary muscle and potentially the zonules via the stabilizing members, the optic can assume a spherical shape in an accommodated state when the ciliary muscle contracts. The optic can assume a flatter shape in an un-accommodated state (also referred to as a non-accommodated state) when the ciliary muscle relaxes and the zonules, which are interdigitated to the haptics via the stabilizing members, are under tension.

An IOL can also include carrier 44 comprising body 46 having anterior face 48, posterior face 50, and interior channel 52 in fluid communication with right aperture 54 and left aperture 56. Right aperture 54 can be sized and dimensioned to receive medial end 24 of right haptic 20 and left aperture 56 can be sized and dimensioned to receive medial end 36 of left haptic 32 as illustrated in FIG. 5. Body 46 can define opening 58 extending substantially parallel to optical axis OA and sized and dimensioned to receive optic 12. As seen in FIG. 5, the medial ends 24 and 36 of the right haptic and the left haptic can mate with apertures 54 and 56 respectively such that a seal is formed between the two components to prevent the entry of fluid into the interior channel of the carrier. Alternatively or additionally, an elastic or flexible biocompatible membrane can cover the medial ends of the right haptic and the left haptic that is connected to the sleeve and the translating arm respectively to avoid fibrosis and restriction of the moveable elements of the IOL. Similarly, optic 12 can mate with opening 58 of carrier 44 such that a seal is formed between the two components to prevent the entry of fluid into the interior chamber of the carrier. The posterior face of the carrier may also contain a fixed optical lens power, either spherical, cylindrical, spherocylindrical, and/or aspheric power.

Figure 2:
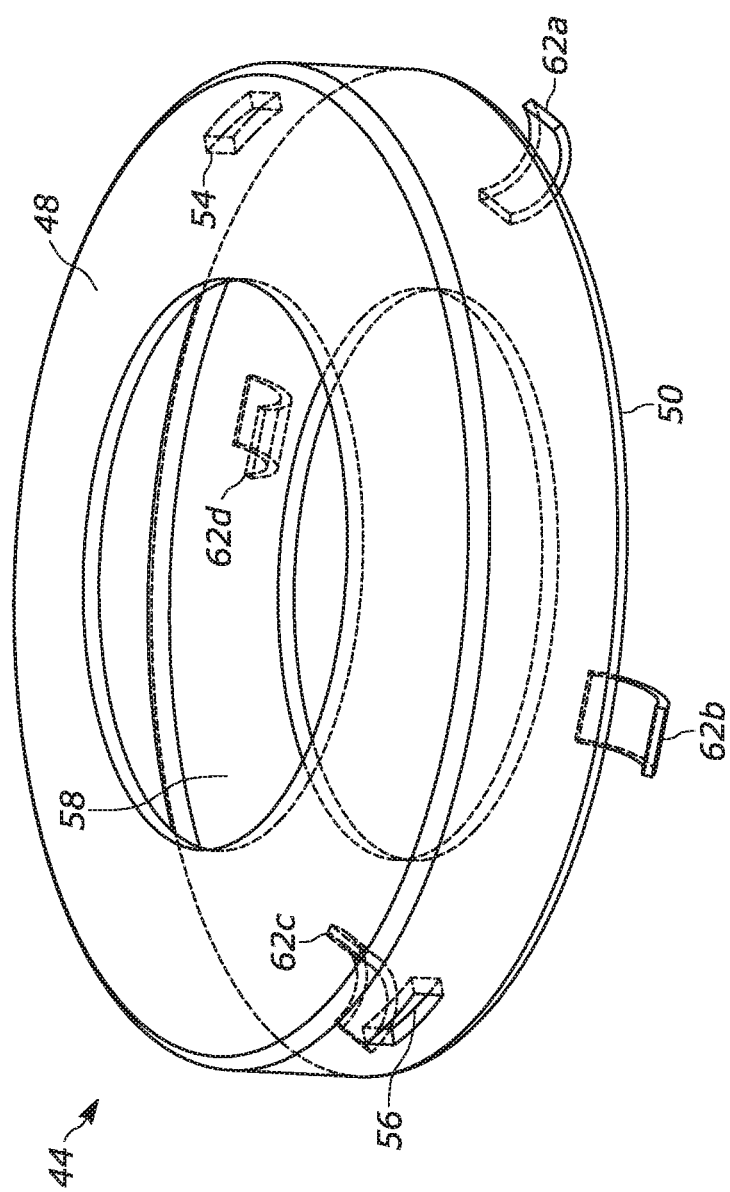
FIG. 2 is a perspective view of an embodiment of a carrier of an IOL according to an aspect of the present disclosure.
Figure 3:
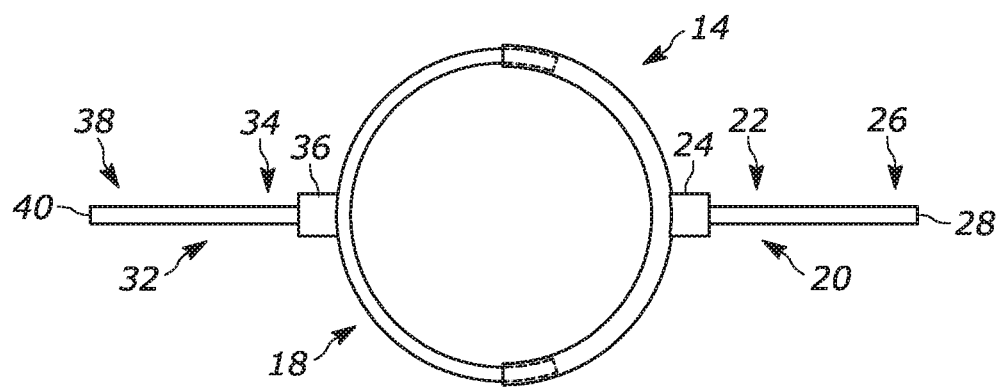
FIG. 3 is a top view of an embodiment of a translating arm, a sleeve, a right haptic, and a left haptic of an IOL according to an aspect of the present disclosure.
Figure 6:
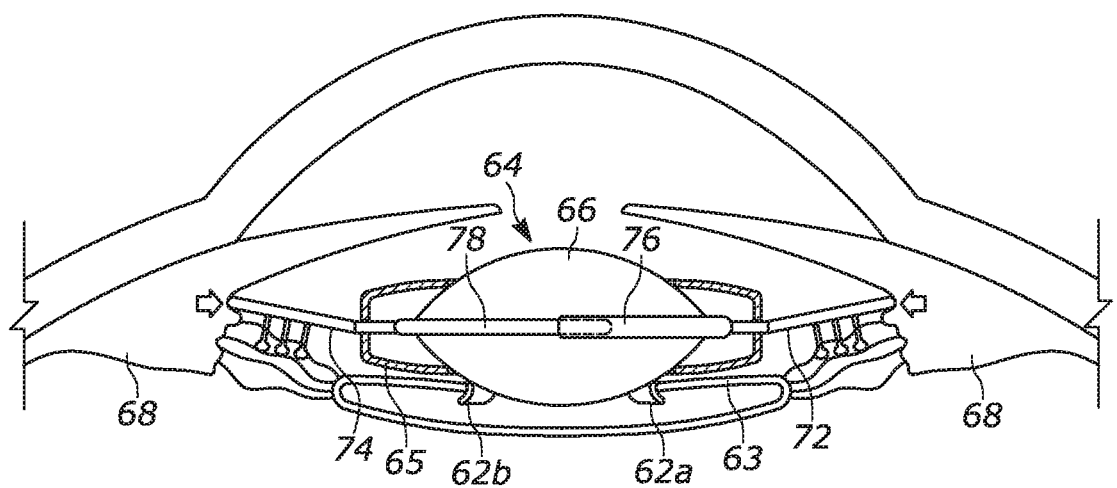
FIG. 6 is a side view of an embodiment of an IOL placed in a patient's eye when the optic of the IOL assumes an accommodated state according to an aspect of the present disclosure.
Figure 7:
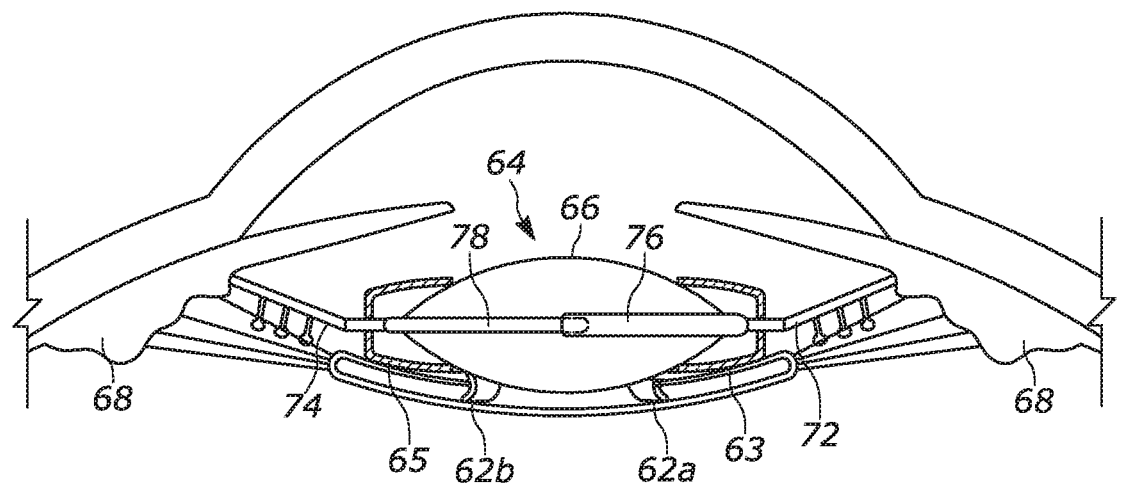
FIG. 7 is a side view of the embodiment of the IOL illustrated in FIG. 6 when the optic of the IOL assumes an un-accommodated state according to an aspect of the present disclosure.

The carrier can have one or more centration lips 62 disposed on posterior face 50 to fixate the carrier into the anterior and/or posterior lens capsule 63 of the patient's eye to allow fixation and centration within a capsulotomy (either an anterior capsulotomy, posterior capsulotomy, or both) as shown in FIGS. 6 and 7. The centration lip can be, for example, a clip or other fixation structure that allows the IOL to engage with the lens capsule without damaging the lens capsule and to center the optic in a capsulotomy opening. To further ensure that the optic remains centered in a capsulotomy opening, the one or more centration lips can be circumferentially spaced about the posterior face of the carrier as illustrated in FIG. 2 in the case of more than one centration lip. The one or more centration lips can include at least two centration lips equidistantly spaced part from one another. Alternatively, the centration lip can extend circumferentially without space in the case of one centration lip, such as a single circumferential lip, which can be a one-piece lip integral with the carrier. Fixation within the capsulotomy opening can allow haptic movement to occur without the optic being pushed, or drawn, off center with ciliary muscle contraction or relaxation. With the optic being pushed or pulled from opposing sides, the optic may likely move side-to-side if resistance or pressure on one haptic is different than resistance or the pressure on the opposing haptic differs. Keeping the optic centered allows for balance and optical centration which enhances the visual performance of the IOL. This is true for all IOLs especially multi focal, diffractive and EDF IOLs.

Such a centration lip can be implemented with IOLs as described herein or with respect to other IOLs. With the recent capability of creating a precise sized capsulotomy opening with either thermal energy or femtosecond laser, for example, achieving and maintaining precise centration of an IOL optic is possible with such a centration lip. Such a centration lip can be important for pseudo accommodating IOLs (e.g. multifocal, diffractive, and EDF lenses) that achieve best functionality when centration is precise and maintained. As described in detail below, such a centration lip can be placed on the anterior face or the posterior face of an IOL. Such a centration lip can be directly attached or incorporated into an IOL without requiring a separate carrier as described below.

Figure 30:
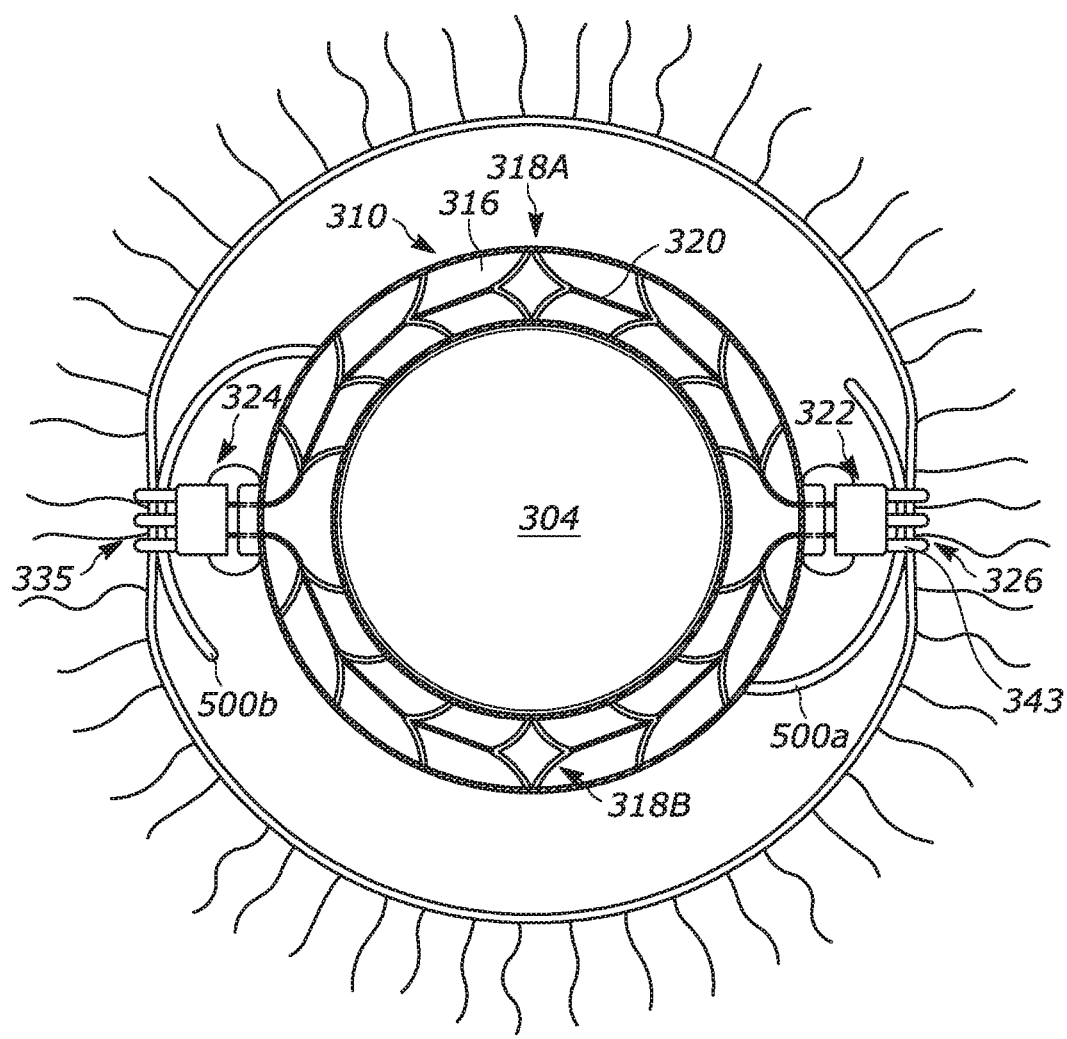
FIG. 30 is a top view an embodiment of an IOL including internal components that illustrates the shape of the lens capsule when the optic assumes an accommodated state.

IOLs as described herein can be placed anterior to an existing, previously placed IOL and could be of such power as to correct any residual refractive error and also provide accommodation near focus. A problem with lenses placed in the capsular bag is that the lens and more specifically the lens optic can separate the anterior and posterior elements of the lens capsular bag. This can allow residual peripheral cells (which are often never completely removed with cataract surgery) to grow across the posterior lens capsule (and sometimes the anterior lens capsule as well). This can produce cloudiness (referred to as "posterior capsule opacification") that can interfere with vision. Posterior capsule opacification can require further laser treatment to "open" the posterior capsule and clear the vision. This laser treatment can not only be costly, but can cause complications including glaucoma, retinal detachment, etc. Attempts to mitigate this have included squaring the edge of the optic to "block" the cells from migrating into the visual axis. However, a more effective way of preventing this is if the anterior lens capsule is sealed to the posterior lens capsule. When these membranes seal together, the peripheral cells cannot migrate into the visual axis. A way of achieving the sealing of the anterior and posterior membranes of the capsule can be to implant an IOL with a centration member as described above, such as two or more small hooks, which can engage with the lens capsular bag and also center the optic in the anterior capsular opening. Haptics can extend from at least two of these hooks to engage the capsular bag as shown in FIG. 30, for example, described in more detail below. The optic can be positioned anterior to the anterior capsule and not within the capsular bag. An advantage of this embodiment is that the anterior and posterior lens capsule can seal together thus preventing posterior capsular opacification. Such an embodiment can be used for patients who have already had cataract surgery with a fixed power lens implant and need to wear bifocal or reading glasses. With such an embodiment, an IOL with a low power optic with power to correct any residual refractive error and can be placed anterior to the already implanted IOL to allow the patient to have accommodated vision and mitigate the need for reading glasses.

The posterior face of the carrier can be open in an embodiment or closed in another embodiment to provide a fixed dioptric and/or astigmatic power. In other words, the posterior face of the carrier can have various spherical/aspheric as well as cylindrical shapes to provide fixed dioptric or astigmatic power(s). The carrier can be fabricated from suitable sterile biocompatible materials such as, for example, silicone, acrylic, polymethylmethacrylate, polyurethane, and suitable combinations thereof.

FIGS. 6-7 provide a schematic illustration of an embodiment of an implanted IOL 64 with carrier 65 and the surrounding ocular anatomy when the optic 66 assumes an accommodated state and an un-accommodated state, respectively. Referring to FIG. 6, which illustrates optic 66 in an accommodated state, when ciliary muscle 68 contracts, the circumferential pressure of ciliary muscle 68 (indicated by the arrows) is translated into linear pressure applied through right and left haptics 72 and 74 to sleeve 76 and translating arm 78 respectively. This results in translating arm 78 and sleeve 76 moving closer together with translating arm 78 gliding in a medial direction in the lumen of sleeve 76. This linear pressure translates back into circumferential pressure on optic 66 reducing the diameter of the optic. This causes optic 66 to assume a more spherical shape resulting in increased focusing power of optic 66 (e.g. optic 66 assumes an accommodated state). Referring to FIG. 7, which illustrates optic 66 in an un-accommodated state, when ciliary muscle 68 relaxes, optic 66 is pulled into a flatter shape by the outward tension on right haptic and left haptic 72 and 74 causing translating arm 78 to pull outward on optic 66, flattening optic 66. As can be seen from FIG. 7, the outward tension on right haptic and left haptic 72 and 74 causes translating arm 78 to glide in a lateral direction in the lumen of sleeve 76. The haptics can be placed outside of the lens capsule and positioned in the ciliary sulcus against the ciliary muscle, for example. Such an embodiment can be implemented in patients that have an already implanted IOL or patients that do not have an already implanted IOL.

Figure 8:
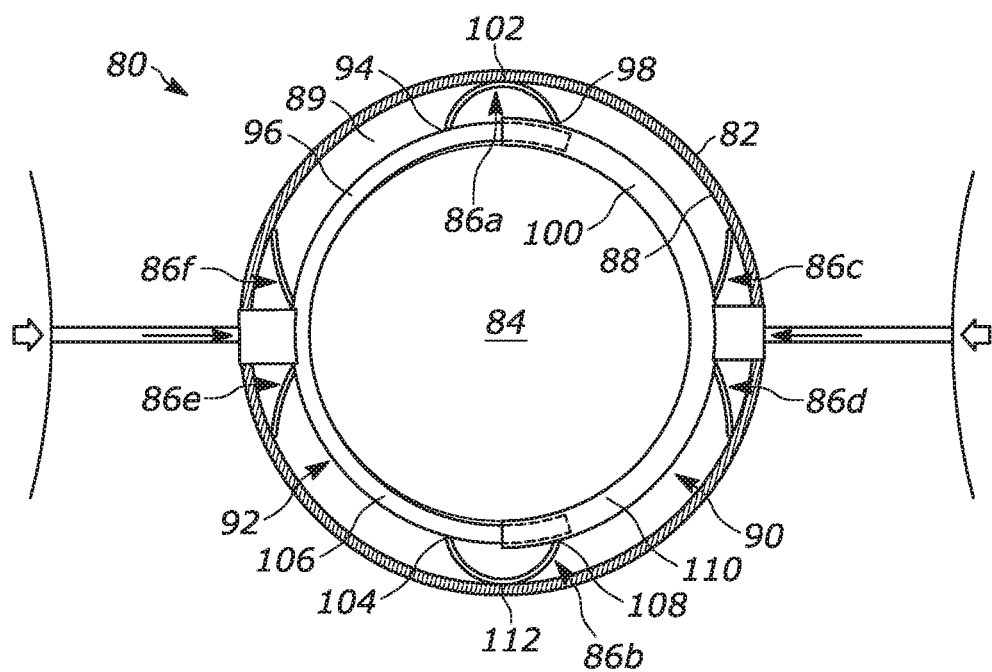
FIG. 8 is top view of an embodiment of an IOL depicting internal components of the IOL when the optic of the IOL assumes an accommodated state according to an aspect of the present disclosure.
Figure 9:
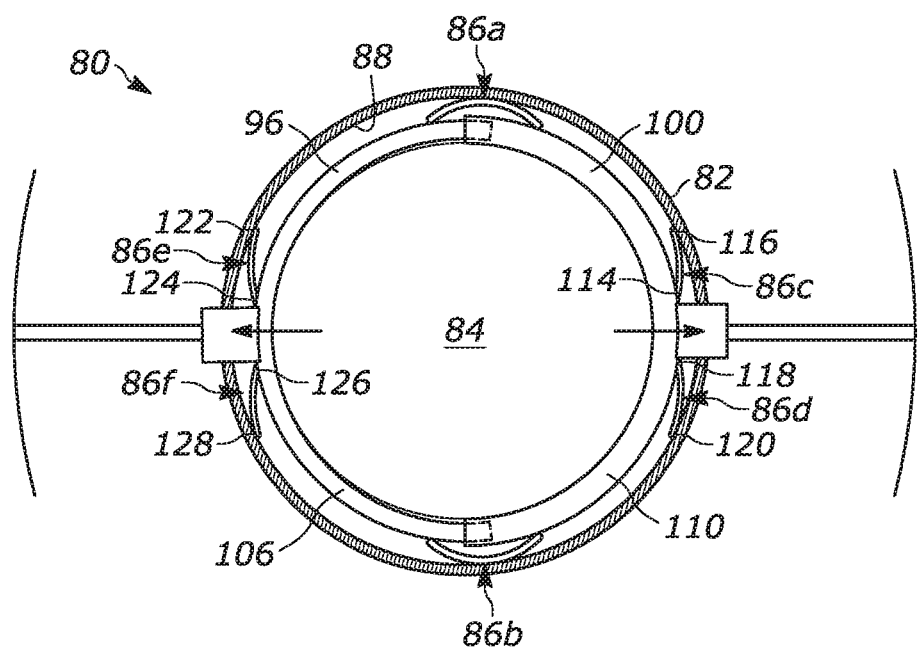
FIG. 9 is a top view of the embodiment of the IOL illustrated in FIG. 8 when the optic of the IOL assumes an un-accommodated state according to an aspect of the present disclosure.

FIGS. 8 and 9 are top views of an IOL 80 illustrating internal components of an embodiment of carrier 82 when optic 84 is in an accommodated state and an un-accommodated state, respectively. In particular, IOL 80 can comprise a plurality of springs 86 spaced substantially equidistant within internal channel 89 of carrier 82. Each of the plurality of springs 86 are attached to interior surface 88 of carrier 82 and either or both of sleeve 90 and translating arm 92. For example, IOL can comprise a set of opposing front and back springs 86a and 86b, each connected at three sites: a site of a translating arm segment, a site of a sleeve segment, and a site of interior surface of the carrier between the sites of the translating arm segment and the sleeve segment. In particular, front spring 86a can be connected to site 94 of first translating arm segment 96, site 98 of first sleeve segment 100, and site 102 of interior surface 88 of carrier 82 between sites 94 and 98. Similarly, back spring 86b can be connected to site 104 of second translating arm segment 106, site 108 of second sleeve segment 110, and site 112 of interior surface 88 between sites 104 and 108. Alternatively or additionally, the plurality of springs 86 can include opposing right and left sets of springs. As shown in FIG. 9, the set of opposing right springs 86c and 86d can each be connected at two sites: a site of a translating arm segment or a sleeve segment and a site of the interior surface of the carrier. In particular, as depicted in FIG. 9, spring 86c can be connected to site 114 of first sleeve segment 100 and site 116 of interior surface 88 of carrier 82. Similarly spring 86d can be connected to site 118 of second sleeve segment 110 and site 120 of the interior surface 88 of carrier 82. The set of opposing left springs 86e and 86f can each be connected at two sites: a site of a translating arm segment and a site of the interior surface of the carrier. In particular, spring 86e can be connected to site 124 of first translating arm segment 96 and site 122 of interior surface 88 of carrier 82. Similarly spring 86f can be connected to site 126 of second translating arm segment 106 and site 128 of interior surface 88 of carrier 82.

The plurality of springs can provide increased resistance to the inward movement of the haptics with ciliary muscle contraction such that the springs bow inward and assume a loaded configuration as the haptics move towards each other as schematically illustrated in FIG. 8. This allows for the translating arm and sleeve to be pushed apart (flattening the optic) and pushing the haptics up against the ciliary muscle as the ciliary muscle relaxes. When the ciliary muscle contracts, the springs provide increasing resistance such that the increased dioptric power of the optic is proportional and the configuration of the springs can be such as to provide appropriate resistance to control the dioptric power change of the optic.

The haptics assume an unloaded configuration and spring back into a neutral resting position with relaxation of the ciliary muscle as schematically illustrated in FIG. 9. In other words, with peripheral force (contraction of the ciliary muscle) and inward movement of the haptics, the plurality of springs flexes (as illustrated in FIG. 8) and with relaxation of the peripheral force (relaxation of the ciliary muscle), the spring action of the plurality of springs pull the haptics apart (as illustrated in FIG. 9). The haptics can be placed outside of the lens capsule and positioned in the ciliary sulcus against the ciliary muscle, for example. Such an embodiment can be implemented in patients that have an already implanted IOL or patients that do not have an already implanted IOL.

The haptics of an IOL as described herein or with respect to other IOLs can have a variety of different configurations. Right and left haptics can have a planar configuration or an angulated configuration. For example, referring to FIG. 4, right haptic and left haptic 20A and 32A can each have an low angle posterior angulation A with respect to equator E to engage the ciliary muscle of the patient's eye and allow the optic to remain posterior to and reduce contact with the posterior aspect of the patient's iris. Such a configuration of the haptics can be implemented, for example, when an IOL is fixated in the ciliary sulcus or placed in the lens capsular bag of the patient's eye.

Figure 10:
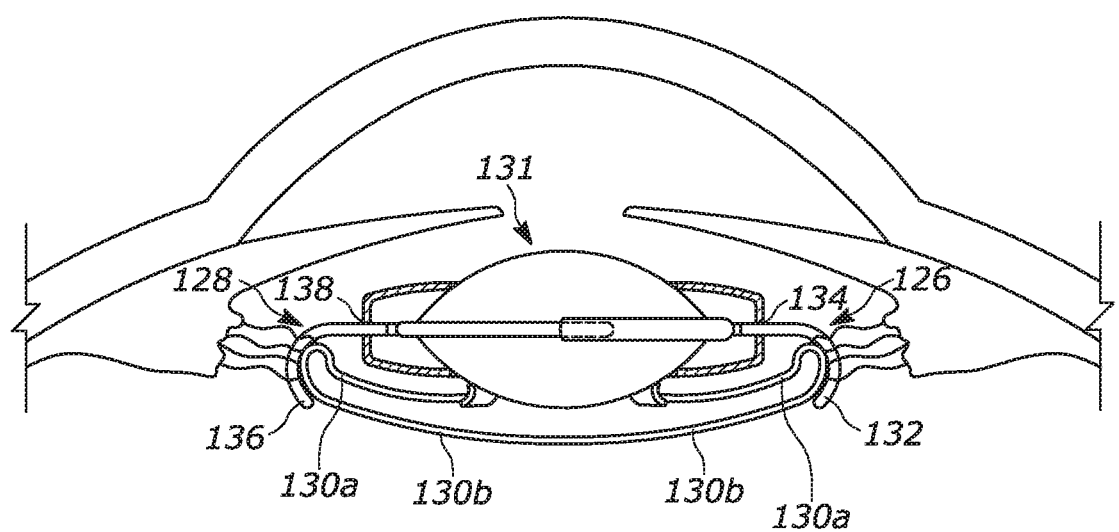
FIG. 10 is a side view of an embodiment of an IOL placed in a patient's eye when the optic of the IOL assumes an accommodated state according to an aspect of the present disclosure.
Figure 11:
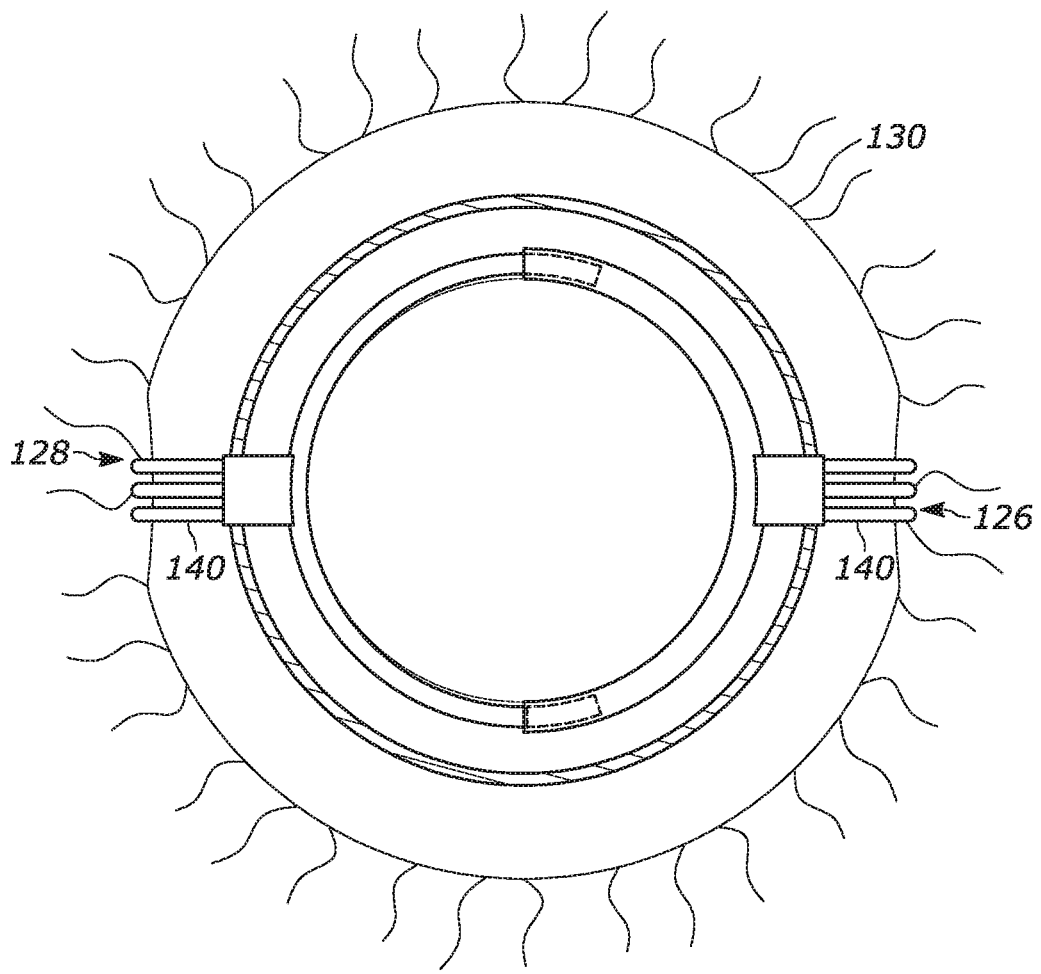
FIG. 11 is a top view an embodiment of an IOL that illustrates the shape of the lens capsule when the optic of the IOL assumes an accommodated state.
Figure 12:
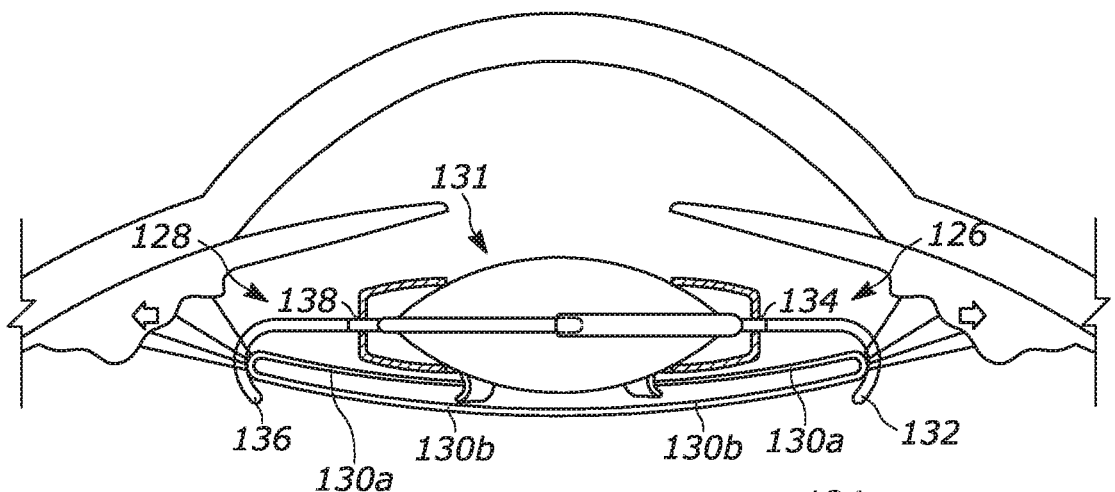
FIG. 12 is a side view of the embodiment of the IOL illustrated in FIG. 10 when the optic of the IOL assumes an un-accommodated state according to an aspect of the present disclosure.
Figure 12A:
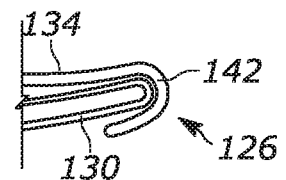
FIG. 12A is a side view of a lateral end of a right haptic according to an embodiment of an IOL of the present disclosure.
Figure 13:
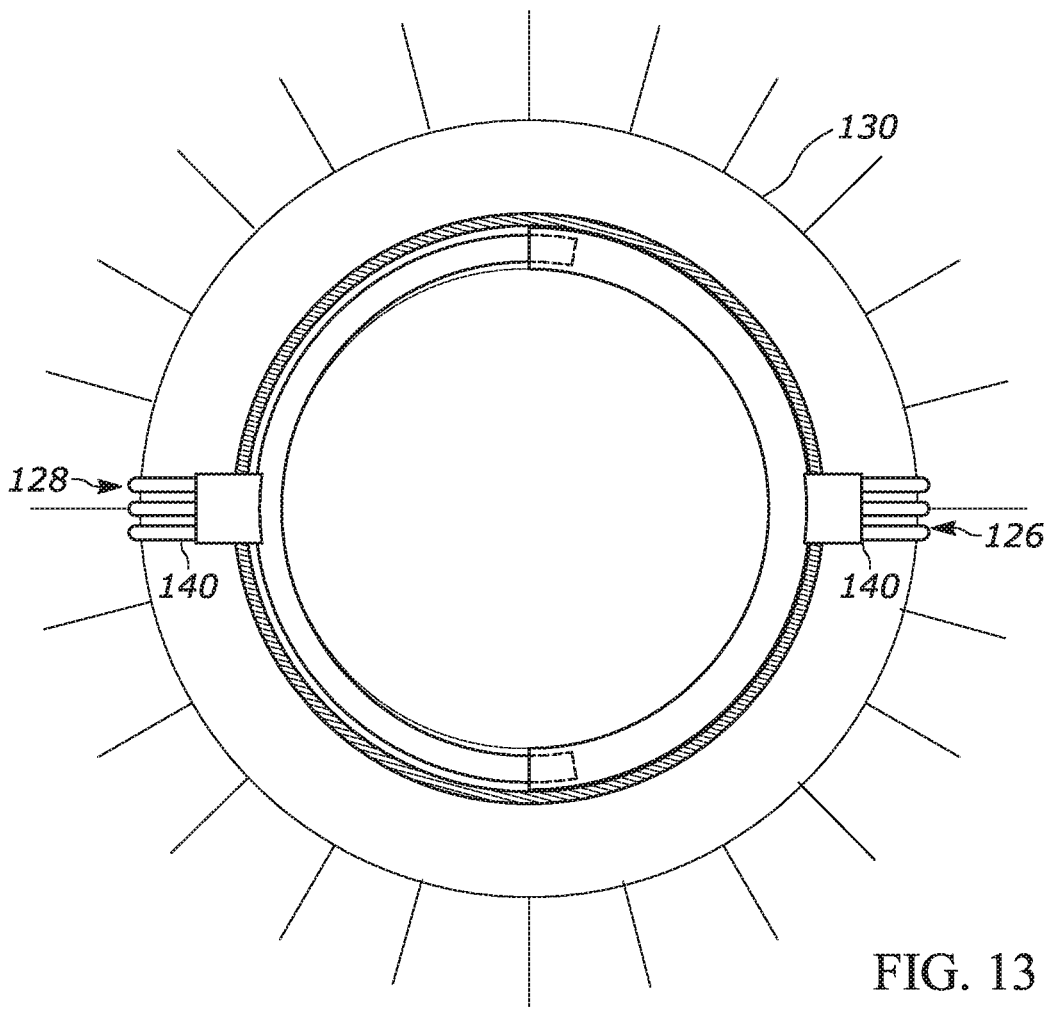
FIG. 13 is a top view an embodiment of an IOL that illustrates the shape of the lens capsule when the optic of the IOL assumes an un-accommodated state.

Referring to FIGS. 10 and 11, right haptic 126 and left haptic 128 of IOL 131 can each have a hook-shaped/substantially J-shaped configuration. In such a configuration, right haptic 126 and left haptic 128 can each curve around anterior lens capsule 130a to posterior lens capsule 130b. In particular, lateral end 132 of right haptic 126 can curve in a posterior direction towards medial end 134 of right haptic 126 and is an atraumatic end so that it does not damage zonules or the lens capsule. Similarly, lateral end 136 of left haptic 128 can curve in a posterior direction towards medial end 138 of left haptic 128 and is an atraumatic end so that it does not damage zonules or the lens capsule. As seen in FIG. 11, left and right haptics 126 and 128 can each comprise a plurality of hooks, such as three hooks 140, for example. In an accommodated state, lens capsule 130 when placed under tension can result in the areas near hooks 140 being pulled inward as seen in FIG. 11. In an un-accommodated state, as illustrated in FIG. 12, lens capsule 130 can be pulled flatter and the entire IOL 130 can shift posteriorly. Right haptic and left haptic and can extend laterally or posterolaterally and then can extend anteriorly having an anterior curvature around anterior lens capsule. In particular, as depicted in FIG. 12A, lateral end 132 of right haptic 126 can extend in a posterolateral direction, then can extend in an anterior direction and have an anterior curvature around anterior lens capsule at portion 142 of right haptic 126, and then can curve in a posterior direction towards medial end 134 of right haptic 126. Left haptic 128 can have a similar configuration. For instance, lateral end 136 of left haptic 128 can extend laterally or posterolaterally, then can extend in an anterior direction, and then can curve in a posterior direction towards medial end 138 of left haptic 128. As seen in FIG. 13, lens capsule 130 can have a more uniform shape as the entire lens capsule is under tension in an un-accommodated state. Hook or substantially J-shaped haptics can allow an IOL to use the force translated from the ciliary muscle to the lens capsule, via the lens zonules, without requiring placement of haptics against elements of the ciliary muscle. Such an embodiment can avoid known potential complications of haptics placed against the ciliary muscle, such as uveitis, glaucoma, and bleeding (e.g. hyphema). Such an embodiment can be implemented in patients that have an already implanted IOL or patients that do not have an already implanted IOL.

Figure 14:
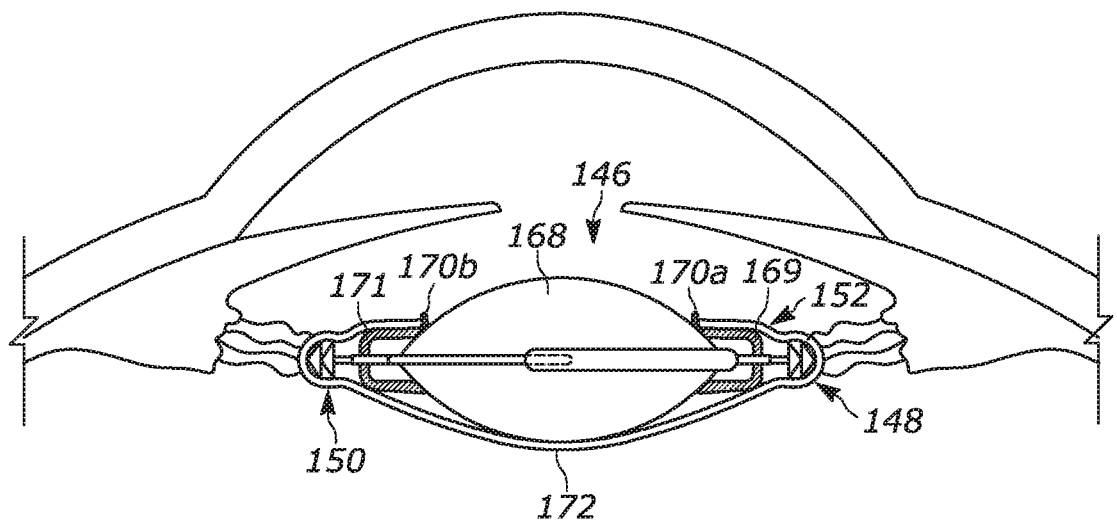
FIG. 14 is a side view of an embodiment of an IOL placed in the patient's eye when the optic of the IOL assumes an accommodated state according to an aspect of the present disclosure.
Figure 15:
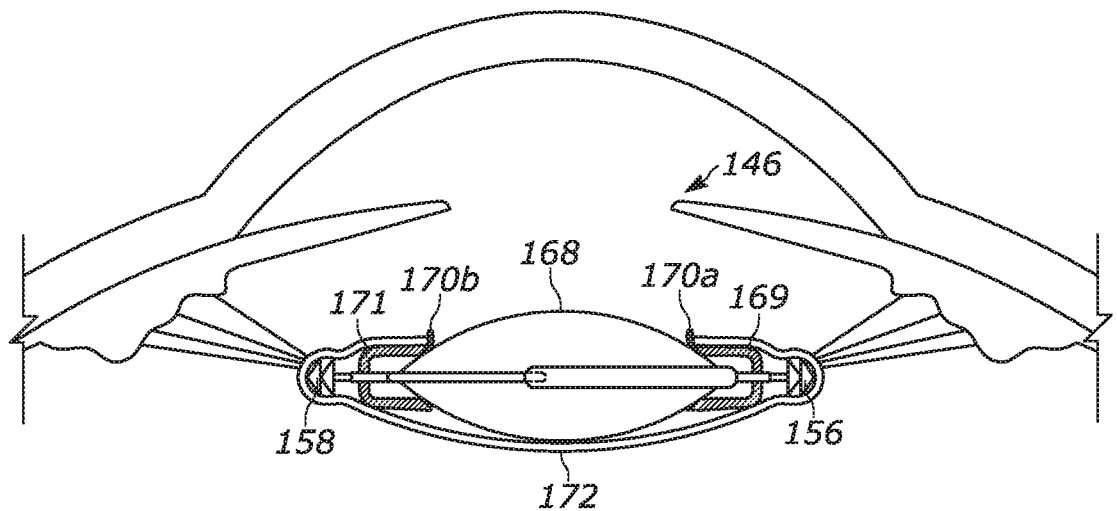
FIG. 15 is a side view of the embodiment of the IOL illustrated in FIG. 14 when the optic of the IOL assumes an un-accommodated state according to an aspect of the present disclosure.
Figure 16:
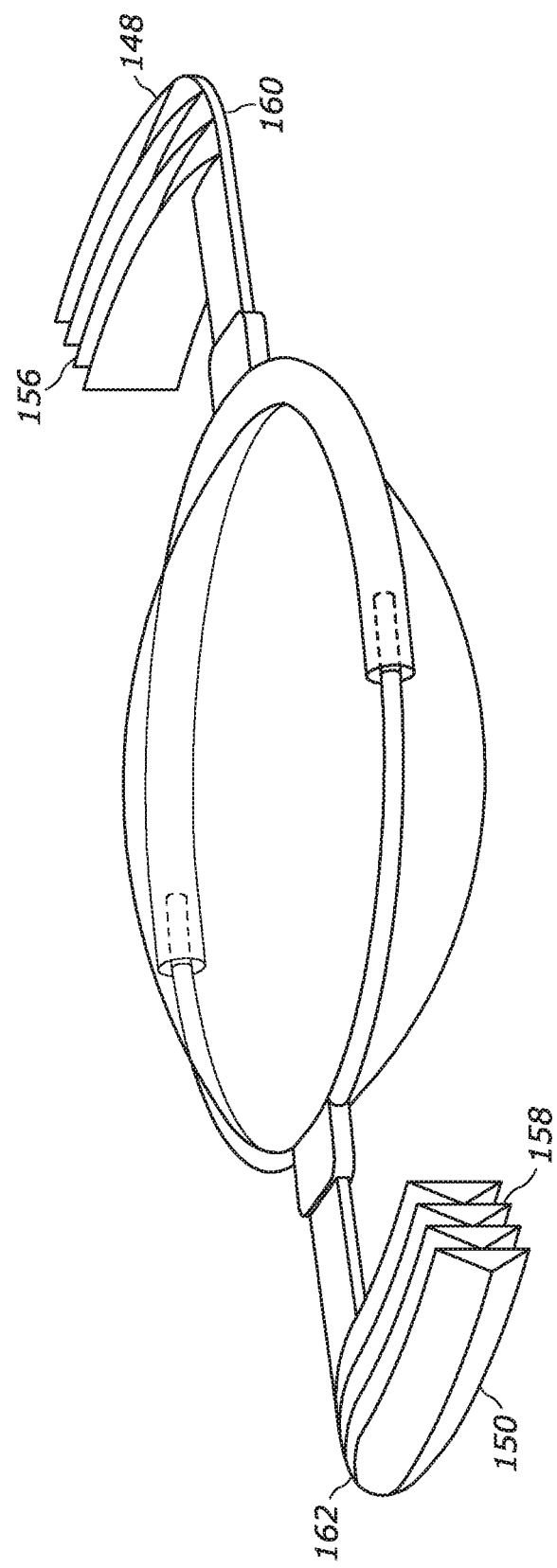
FIG. 16 is a perspective view of an embodiment of an IOL or components of an IOL according to an aspect of the present disclosure.
Figure 17:
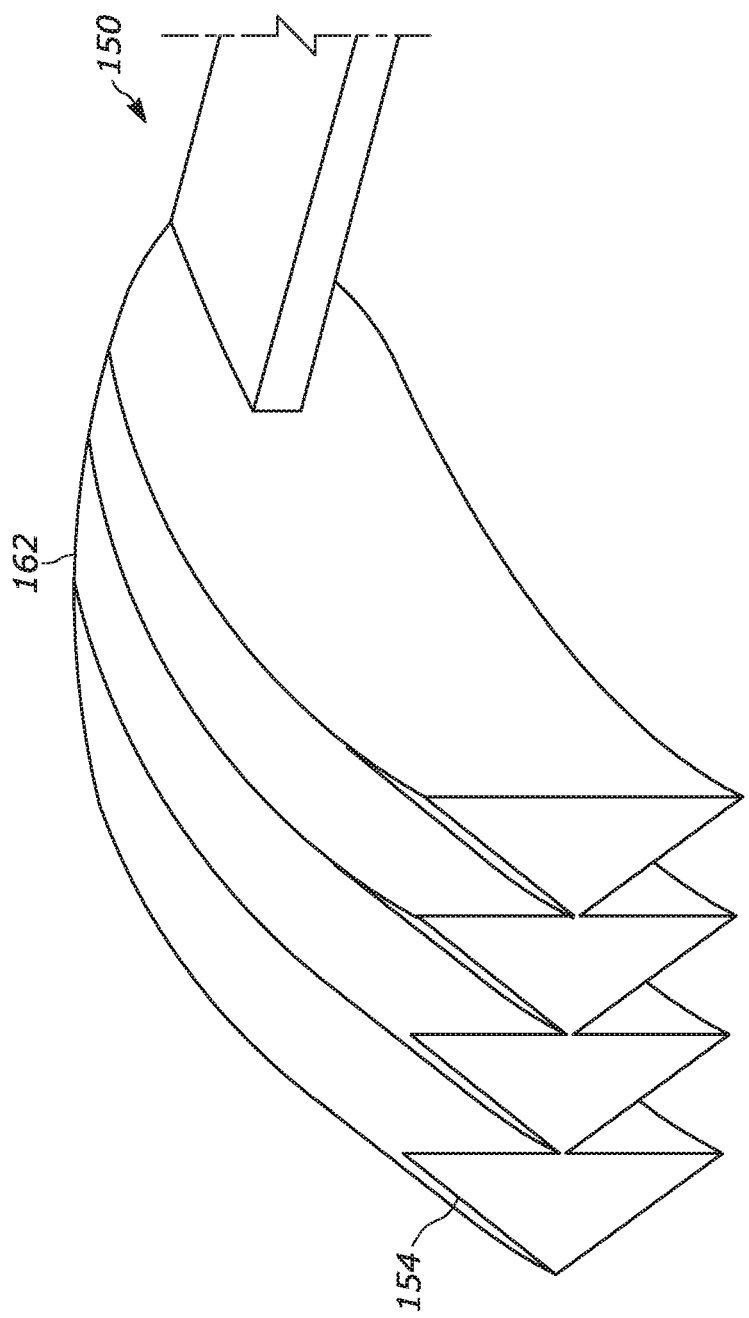
FIG. 17 is partial view of the lateral portion of the left haptic illustrated in FIG. 16 according to an aspect of the present disclosure.

Referring to FIGS. 14-15, which illustrate IOL 146 in an accommodated and un-accommodated state respectively, lateral portions 148 and 150 of right haptic and left haptic 152 and 154 can be respective ridges 156 and 158. Ridges 156 and 158 can interact with the peripheral lens capsule 172 to stabilize the haptics within lens capsule. Ridges can also allow the haptics to interact and fixate into the most peripheral area of the lens capsule. Such an embodiment can allow IOL placement within the capsular bag, while still allowing translation of tension/relaxation of the peripheral lens capsule (via the lens zonules and ciliary body) during accommodation/relaxation of the lens. Current haptic designs do not allow the haptics to be positioned into the peripheral lens capsule while fixating the haptics to allow tension/relaxation on the lens capsule to translate forces into the haptics. Current haptic designs are smooth and allow the capsule and haptic to slide past each other, which does not allow the translation of forces placed on the peripheral lens capsule (via the zonules and ciliary muscle). As shown in FIGS. 16-17, leading edges 160 and 162 of lateral portions 148 and 150 can be smooth and narrower than trailing edges 152 and 154 of lateral ends 156 and 158 of respective left haptic and right haptic 152 and 154. In certain embodiments, the portions of the haptics medial to the ridges can be plates. Such a configuration of the haptics can be implemented when the IOL is placed in the lens capsular bag of the patient's eye. When placing the IOL inside the capsular bag, this feature allows the IOL to be rotated (clockwise) and allows the ridged ends of the haptics to rotate until the desired rotational position of the IOL is achieved. Once the IOL is rotated into its desired position, the forces on the haptics fixate lateral portions of the haptics to the inside peripheral edge of the lens capsule. The ridges then provide resistance to these forces and allow the haptics to pull outward against the mechanics of the optic and associated components, be it a spring system, translating arm/sleeve system or compressible fluid system as described herein.

Referring back to FIGS. 14 and 15, carrier 171 can have one or more centration lips 170, such as lips, on an anterior face 168 thereof to keep the optic centered in a capsulotomy opening of a lens capsule 172. Fixation within the capsulotomy opening can allow the movement of the haptics to occur without the optic being pushed, or drawn, off center with ciliary muscle contraction or relaxation. In certain embodiments, the one or more centration lips are a plurality of centration lips spaced about and disposed on the anterior face of the carrier, or could extend circumferentially without spaces such as single circumferential lip integral with the carrier. Such centration lips can be implemented with other IOLs not just those described in the present disclosure. With the recent capability of creating a precise sized capsulotomy opening with either thermal energy or femtosecond laser, for example, achieving and maintaining precise centration of an IOL optic is possible with a centration lip. Such a centration lip can be important for pseudo accommodating IOLs (e.g. multifocal, diffractive, and EDF lenses) that achieve best functionality when centration is precise and maintained. Such a centration lip can also be placed on the anterior surface or the posterior surface of an IOL, as described above. Such a centration lip can be directly attached or incorporated into an IOL without requiring a separate carrier.

Figure 18:
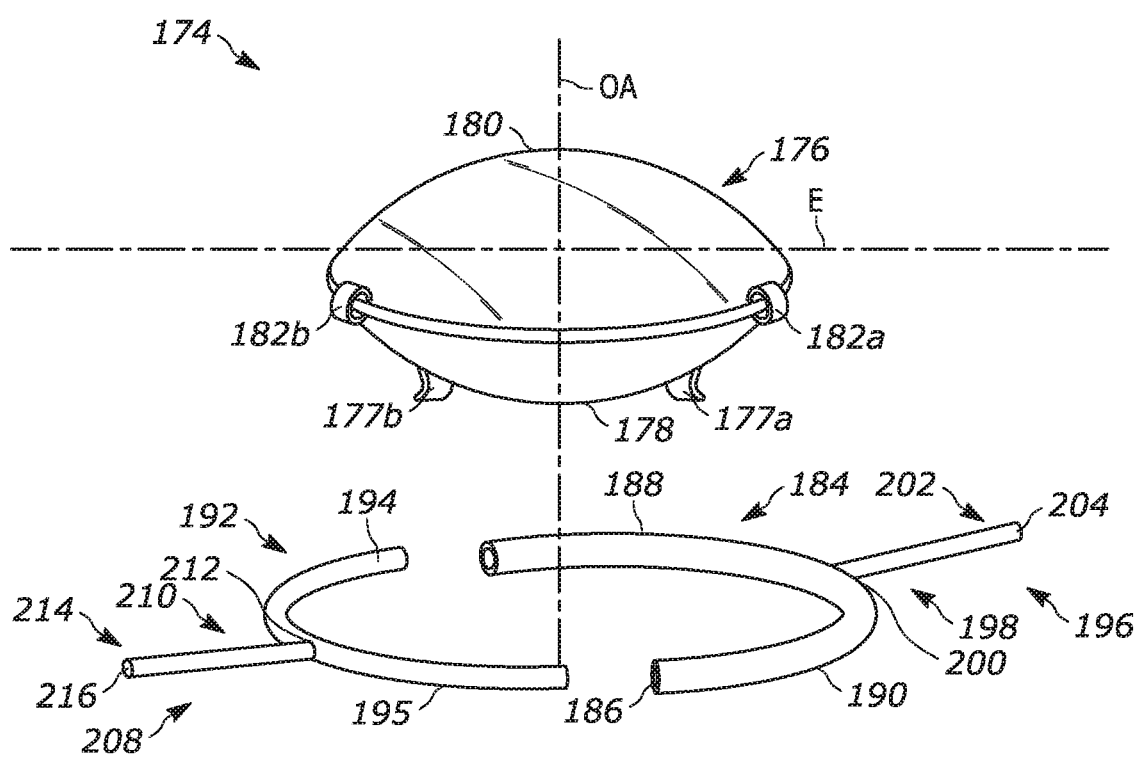
FIG. 18 is an exploded view of an embodiment of an IOL according to an embodiment of the present application.

In certain aspects, an IOL does not include a carrier. For example, referring to FIG. 18, IOL 174 can comprise optic 176 having optical axis OA extending in an anterior-posterior direction, posterior face 178, anterior face 180, and equator E extending in a plane substantially perpendicular to optical axis OA. Optic 176 can have guide 182 disposed thereon. Although FIG. 18 depicts two guides 182, optic 176 can include only one guide or more than two guides, such as a plurality of guides spaced about the equator of the optic, such as equidistantly spaced about the equator, for example. The posterior face of the optic can have various spherical as well as cylindrical shapes to provide fixed dioptric or astigmatic power(s).

The posterior face of the optic can also include one or more centration lips 177 disposed thereon as illustrated in FIGS. 18-20 and 23-24 or other IOLs. Centration lips 177 can fixate the optic into the anterior and/or posterior lens capsule 179 of the patient's eye to allow fixation within a capsulotomy (either an anterior capsulotomy, posterior capsulotomy, or both) as shown in FIGS. 19-20 and 23-24. The centration lip can be, for example, a clip or other fixation structure that allows the IOL to engage with the lens capsule without damaging the lens capsule and to center the optic in a capsulotomy opening. To further ensure that the optic remains centered in a capsulotomy opening, the centration lip can be circumferentially spaced about the posterior and/or anterior face of optic such as equidistantly spaced about the circumference of the posterior face, for example, or extend circumferentially without spaces, such as a circumferential lip for example. The one or more centration members can include at least two centration members equidistantly spaced part from one another. Alternatively, the centration member can extend circumferentially without space in the case of one centration member, such as single circumferential lip, which can be a one-piece lip integral with the optic.

In an embodiment, IOL 174 can further includes sleeve 184 disposed about equator E of optic 176 defining lumen 186 and receivable by guide 182. Sleeve can comprise first sleeve segment 188 and second sleeve segment 190. IOL 174 can further include translating arm 192 disposed about equator E of optic 176 opposite sleeve 184 and receivable by guide 182. Translating arm 192 can comprise first translating arm segment 194 glidably receivable by first sleeve segment 188 and second translating arm segment 195 glidably receivable by second sleeve segment 190. The sleeve and translating arms can interact with one another to increase the dioptric power of the optic when the ciliary muscle contracts and the optic lens assumes an accommodated state.

IOL 174 can further include right haptic 196 having medial portion 198 with medial end 200 and lateral portion 202 with lateral end 204. Medial end 200 can be coupled to sleeve 184. Likewise, IOL 174 can also include left haptic 208 having medial portion 210 with medial end 212 and lateral portion 214 with lateral end 216. Medial end 212 can be coupled to translating arm 192. I t is understood that the terms "right" and "left" are only used to identify the haptics and the right haptic could be interchanged with the left haptic such that the right haptic is coupled to the translating arm and the left haptic is coupled to the sleeve. The left and right haptics can include one or more fixation members disposed on a posterior surface thereof to fixate the IOL to surrounding zonules.

Figure 19:
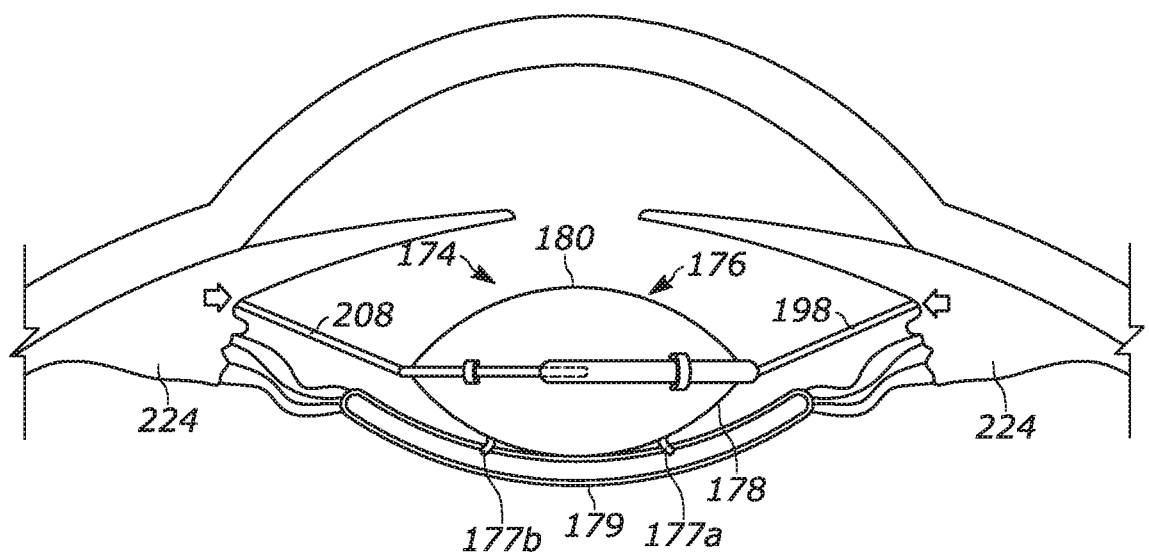
FIG. 19 is a side view of an embodiment of an IOL placed in a patient's eye when the optic of the IOL assumes an accommodated state according to an aspect of the present disclosure.
Figure 20:
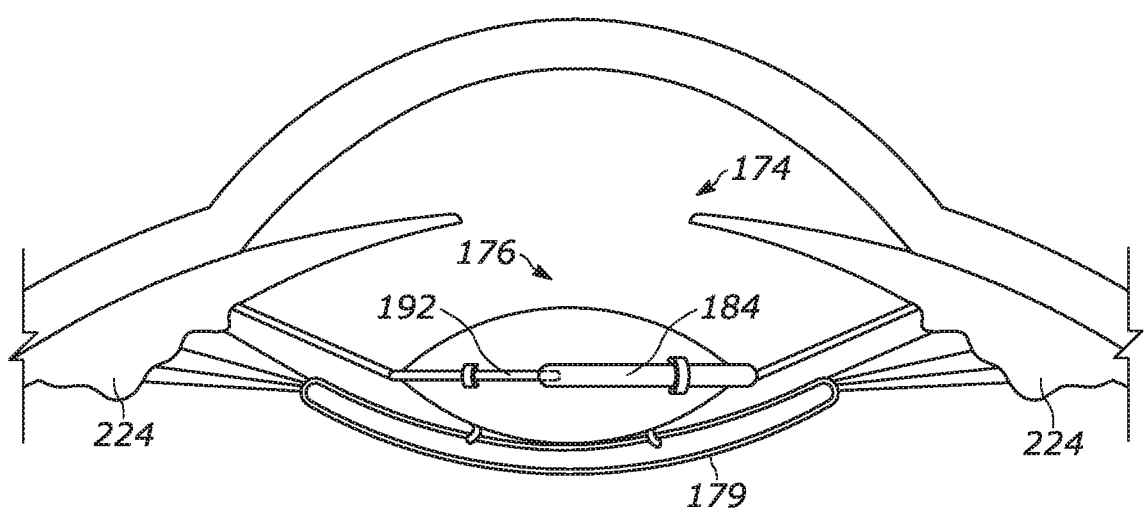
FIG. 20 is a side view of the embodiment of the IOL illustrated in FIG. 19 when the optic of the IOL assumes an un-accommodated state according to an aspect of the present disclosure.

FIGS. 19-20 provide a schematic illustration of an embodiment of implanted IOL 174 and the surrounding ocular anatomy when optic 176 assumes an accommodated state and an un-accommodated state respectively. Referring to FIG. 19, which illustrates optic 176 in an accommodated state, when ciliary muscle 224 contracts, the circumferential pressure of ciliary muscle 224 (indicated by the arrows) can be translated into linear pressure applied through right and left haptics 196 and 208 to sleeve 184 and translating arm 192 respectively. This can result in translating arm 192 and sleeve 184 moving closer together with translating arm 192 gliding in a medial direction in the lumen of sleeve 184. This linear pressure can translate back into circumferential pressure on optic 176 causing optic 176 to assume a more spherical shape resulting in increased focusing power of optic 176 (e.g. optic 176 assumes an accommodated state). Referring to FIG. 20, which illustrates optic 176 in an un-accommodated state, when ciliary muscle 224 relaxes, optic 174 can be pulled into a flatter shape by the outward tension on right and left haptics 198 and 208 causing translating arm 192 to pull outward on optic 176, flattening optic 176. As can be seen from FIG. 20, the outward tension on right haptic and left haptic 198 and 208 can cause translating arm 192 to glide in a lateral direction in the lumen of sleeve 184.

Figure 21:
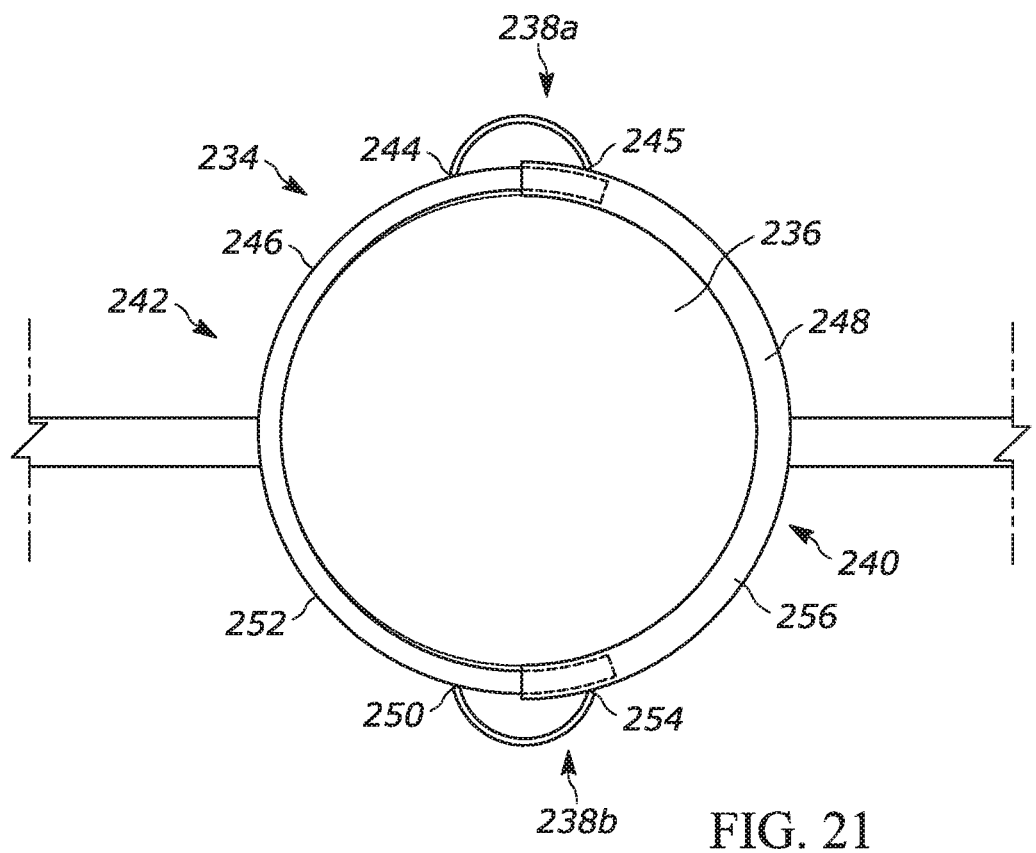
FIG. 21 is top view of an embodiment of an IOL depicting internal components of the IOL when the optic of the IOL assumes an accommodated state according to an aspect of the present disclosure.
Figure 22:
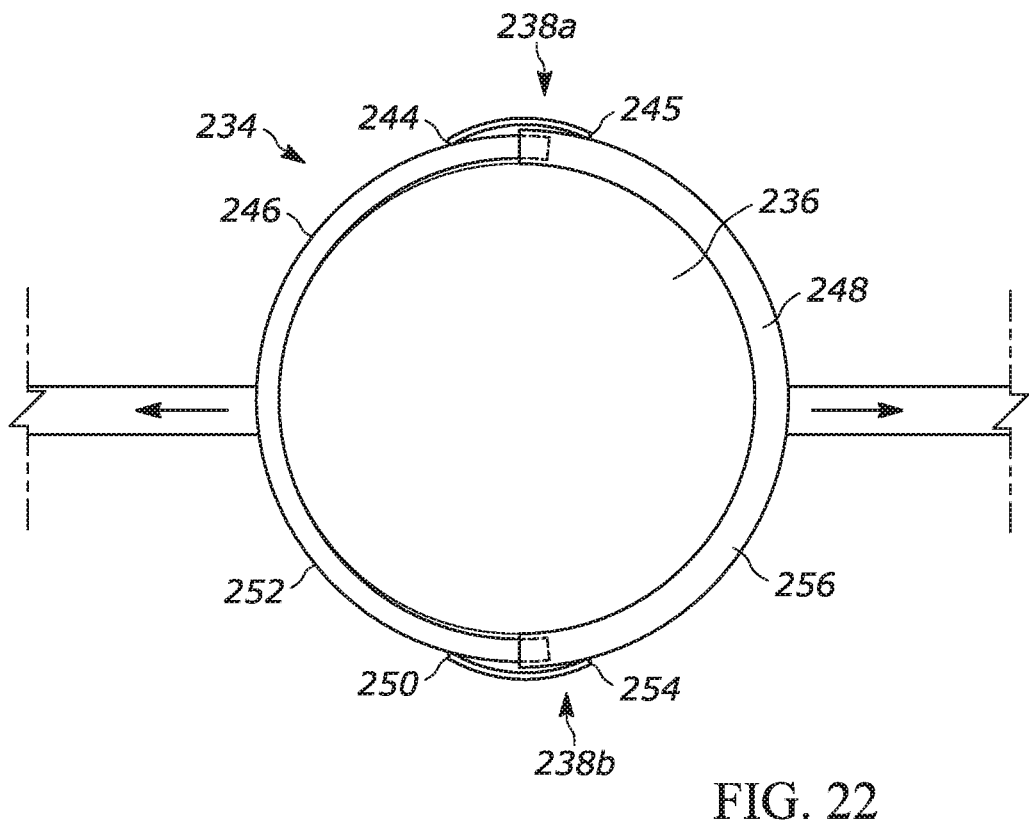
FIG. 22 is a top view of the embodiment of the IOL illustrated in FIG. 21 when the optic of the IOL assumes an un-accommodated state according to an aspect of the present disclosure.

FIGS. 21 and 22 are top views of an IOL 234 when optic 236 is in an accommodated state and an un-accommodated state, respectively. IOL 234 can comprise opposing springs 238 spaced substantially equidistant from each other, each of the opposing springs 238a and 238b attached to a site of the sleeve 240 and a site of the translating arm 242. In particular, spring 238a can be connected to site 244 of the first translating arm segment 246 and site 245 of the first sleeve segment 248. Spring 238b can be connected to site 250 of the second translating arm segment 252 and site 254 of the second sleeve segment 256. Such equidistantly spaced springs can apply substantially equal force to the translating arm and sleeve such that this substantially equal force can be translated to equal circumferential pressure applied to the optic, resulting in a more uniform spherical shape of the optic thereby decreasing optic aberration.

The haptics of an IOL as described herein or with respect to other IOLs can have a variety of different configurations. Right haptic and left haptic 196 and 208 can have a planar configuration or an angulated configuration as shown in FIGS. 19 and 20. For example, left and right haptics can have a low degree posterior angulation with respect to the equator of the optic to engage the ciliary body of the patient's eye and allow the optic to remain posterior to and reduce contact with the posterior aspect of the patient's iris. Such a configuration of the haptics can be implemented, for example, when the IOL is fixated in the ciliary sulcus or placed in the lens capsular bag of the patient's eye. Such an embodiment can be implemented in patients that have an already implanted IOL or patients that do not have an already implanted IOL.

Figure 23:
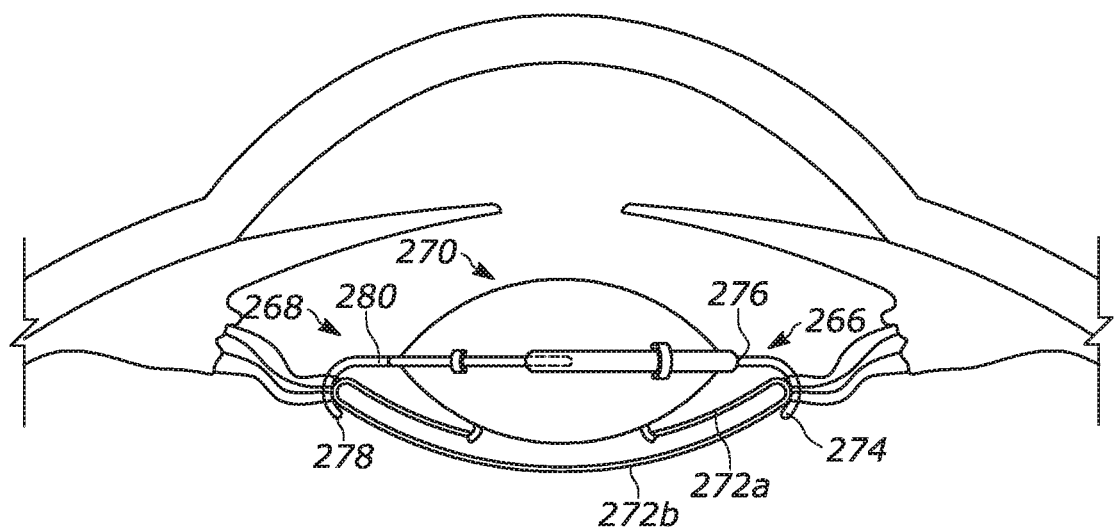
FIG. 23 is a side view of an embodiment of an IOL placed in a patient's eye when the optic of the IOL assumes an accommodated state according to an aspect of the present disclosure.
Figure 24:
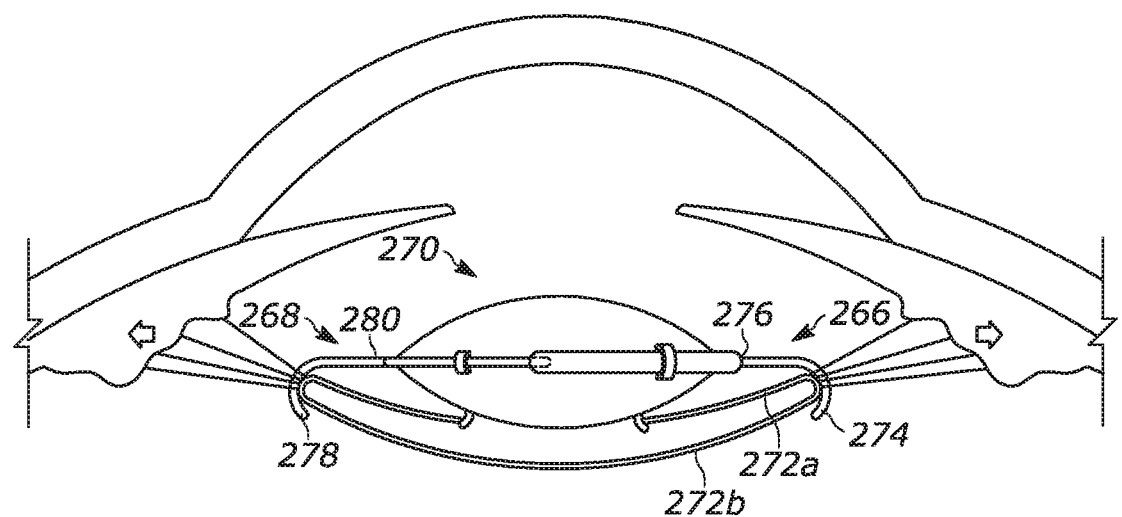
FIG. 24 is a side view of the embodiment of the IOL illustrated in FIG. 23 when the optic of the IOL assumes an un-accommodated state according to an aspect of the present disclosure.

Referring to FIGS. 23 and 24, right haptic 266 and left haptic 268 of an IOL 270 can each have a hook-shaped/substantially J-shaped configuration. In such a configuration, right haptic 266 and left haptic 268 can each curve around anterior lens capsule 272a to posterior lens capsule 272b. In particular, lateral end 274 of right haptic 266 can curve in a posterior direction towards medial end 276 of right haptic 266 and have an atraumatic end so as to not damage zonules or the lens capsule. Similarly, lateral end 278 of left haptic 268 can curve in a posterior direction towards medial end 280 of left haptic 268 and have an atraumatic end so as to not damage zonules or the lens capsule. Left and right haptics 266 and 268 can each comprise a plurality of hook(s), such as three hooks for example, similar to the embodiment illustrated in FIG. 11. In an accommodated state, lens capsule 130 when placed under tension, can result in the areas near the hooks being pulled inward, similar to the configuration of an embodiment of an IOL illustrated in FIG. 11. In un-accommodated state, as illustrated in FIG. 24, lens capsule 272 can be pulled flatter and the entire IOL 270 can shift posteriorly. Right haptic and left haptic 266 and 268 can extend laterally or posterolaterally and then can extend anteriorly having an anterior curvature around anterior lens capsule. In particular, lateral end 274 of right haptic 266 can extend in a lateral or posterolateral direction, then can extend in an anterior direction and then can curve in a posterior direction towards medial end 276 of right haptic 266. Similarly, lateral end 278 of left haptic 268 can extend in a lateral or posterolateral direction, then can extend in an anterior direction, and then can curve in a posterior direction towards medial end 280 of left haptic 268. Lens capsule 272 can have a more uniform shape as the entire lens capsule is under tension in an un-accommodated state. Such a configuration of the haptics can be implemented, for example, when the IOL is fixated in the ciliary sulcus of a patient's eye. Such an embodiment can be implemented in patients that have an already implanted IOL or patients that do not have an already implanted IOL.

Figure 25:
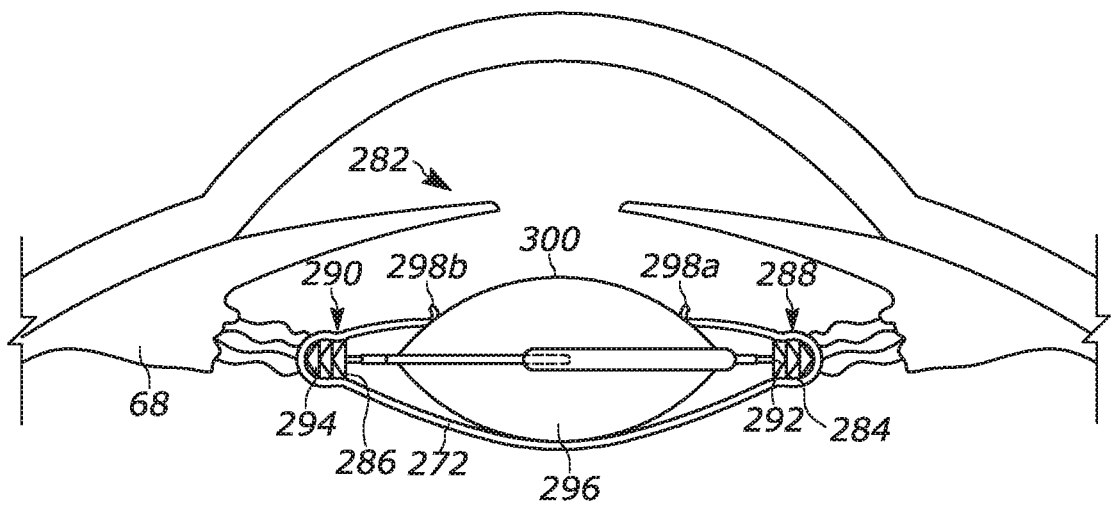
FIG. 25 is a side view of an embodiment of an IOL placed in a patient's eye when the optic of the IOL assumes an accommodated state according to an aspect of the present disclosure.
Figure 26:
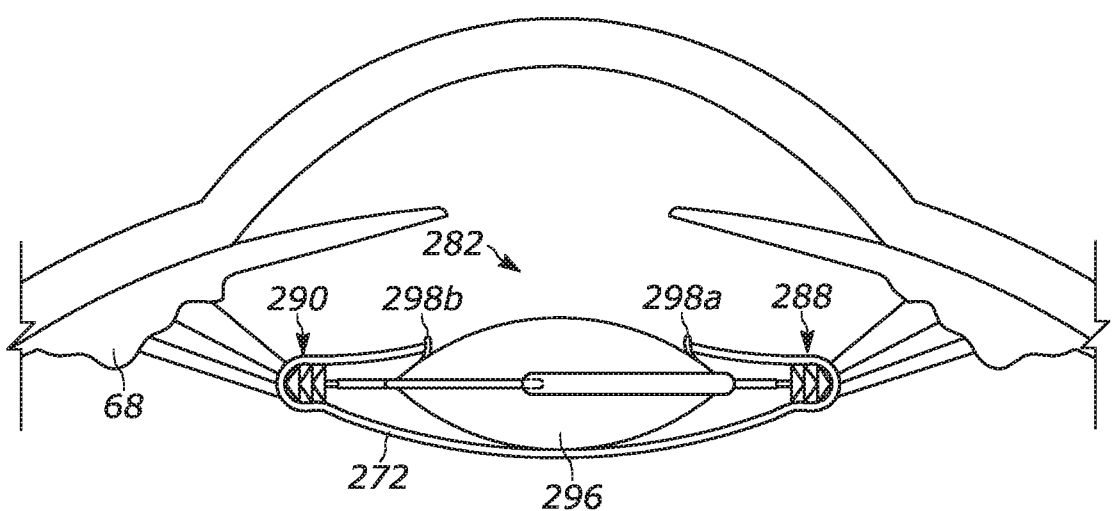
FIG. 26 is a side view of the embodiment of the IOL illustrated in FIG. 25 when the optic of the IOL assumes an un-accommodated state according to an aspect of the present disclosure.

Referring to FIGS. 25 and 26, which illustrate IOL 282 in an accommodated and un-accommodated state respectively, lateral portions 284 and 286 of right and left haptics 288 and 290 respectively can be respective ridges 292 and 294. Ridges 292 and 294 can interact with the peripheral lens capsule to stabilize the haptics within lens capsule. Similar to the embodiment illustrated in FIGS. 16-17, the leading edges of the lateral portions of the right haptic and the left haptic can be smooth and narrower than the trailing edges and of the lateral ends of the respective right haptic and left haptic. In certain embodiments, the portions of the haptics medial to the ridges can be plates. As shown in FIGS. 25-26, optic 296 can comprise at least one centration lip 298 on an anterior face 300 thereof to keep optic 296 centered in lens capsule 272. In certain embodiments, the one or more centration lips are a plurality of centration lips spaced about and disposed on the anterior face of the optic, such as, for example, circumferentially spaced on the anterior surface of the optic. In other embodiments, the centration lip is not spaced apart but is a single centration lip extending about the circumference of the anterior face of the optic, such as, for example, a single centration lip integral with the optic. A centration lip can be implemented in IOLs as disclosed herein as well as other IOLs.

Figure 27:
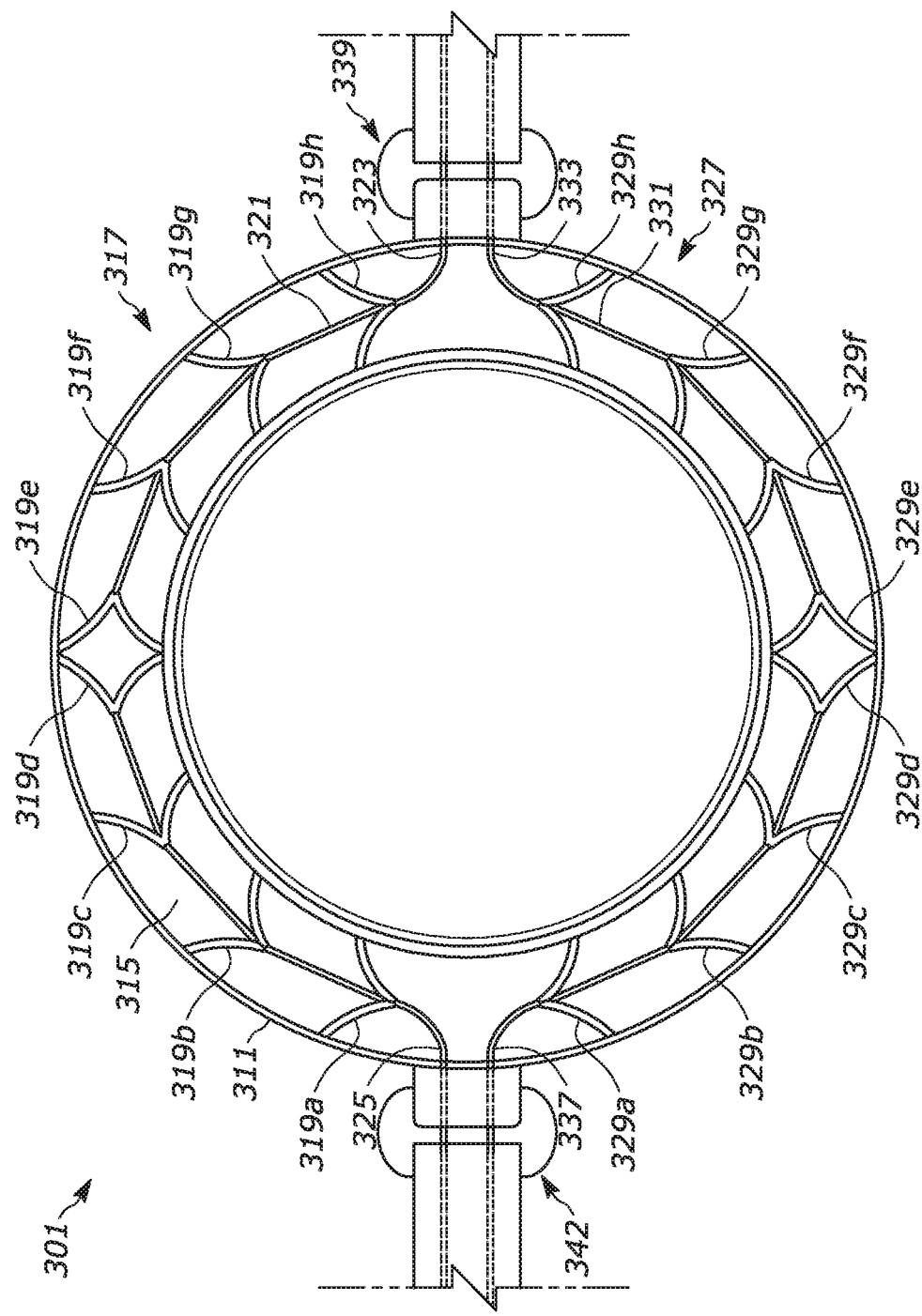
FIG. 27 is top view of an embodiment of an IOL depicting internal components of the IOL when the optic of the IOL assumes an accommodated state according to an aspect of the present disclosure.
Figure 28:
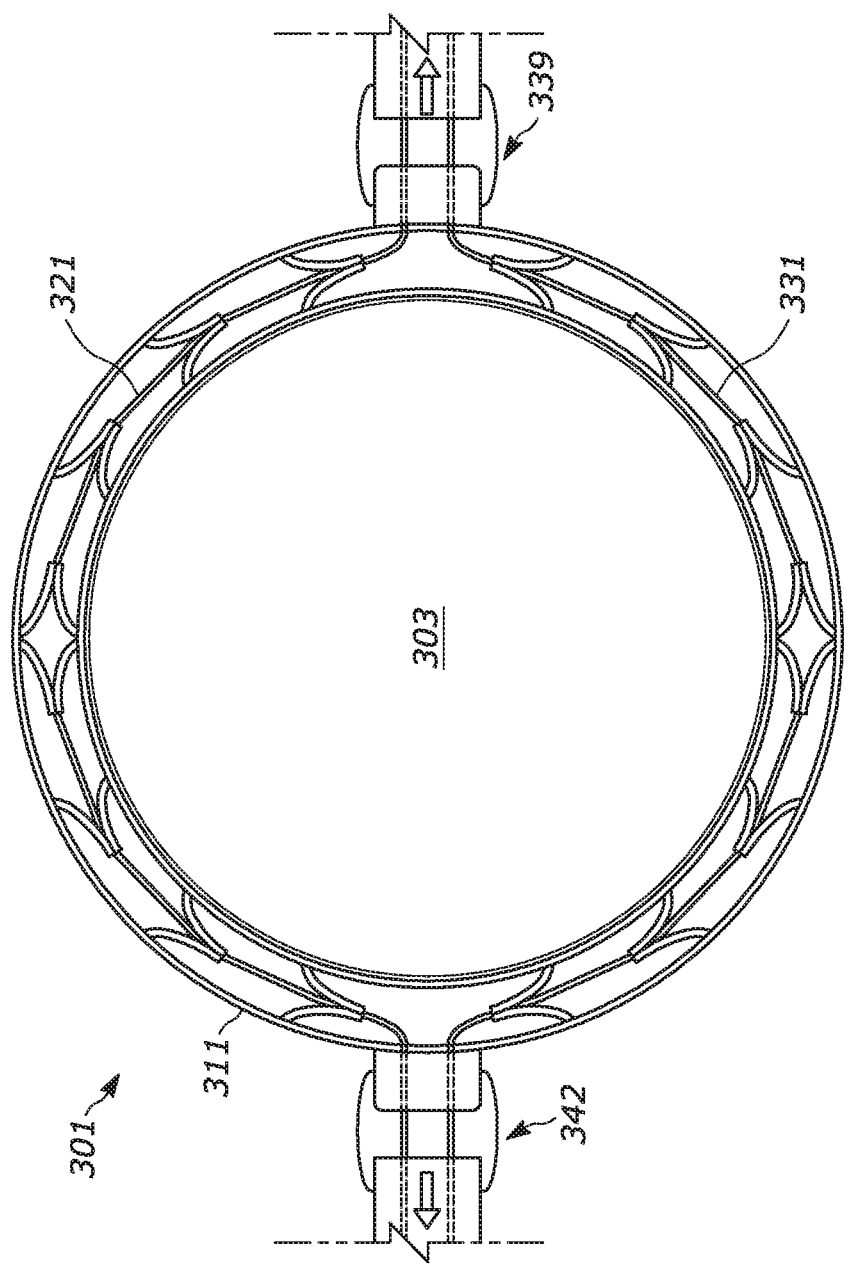
FIG. 28 is a top view of the embodiment of the IOL illustrated in FIG. 27 when the optic of the IOL assumes an un-accommodated state according to an aspect of the present disclosure.
Figure 29:
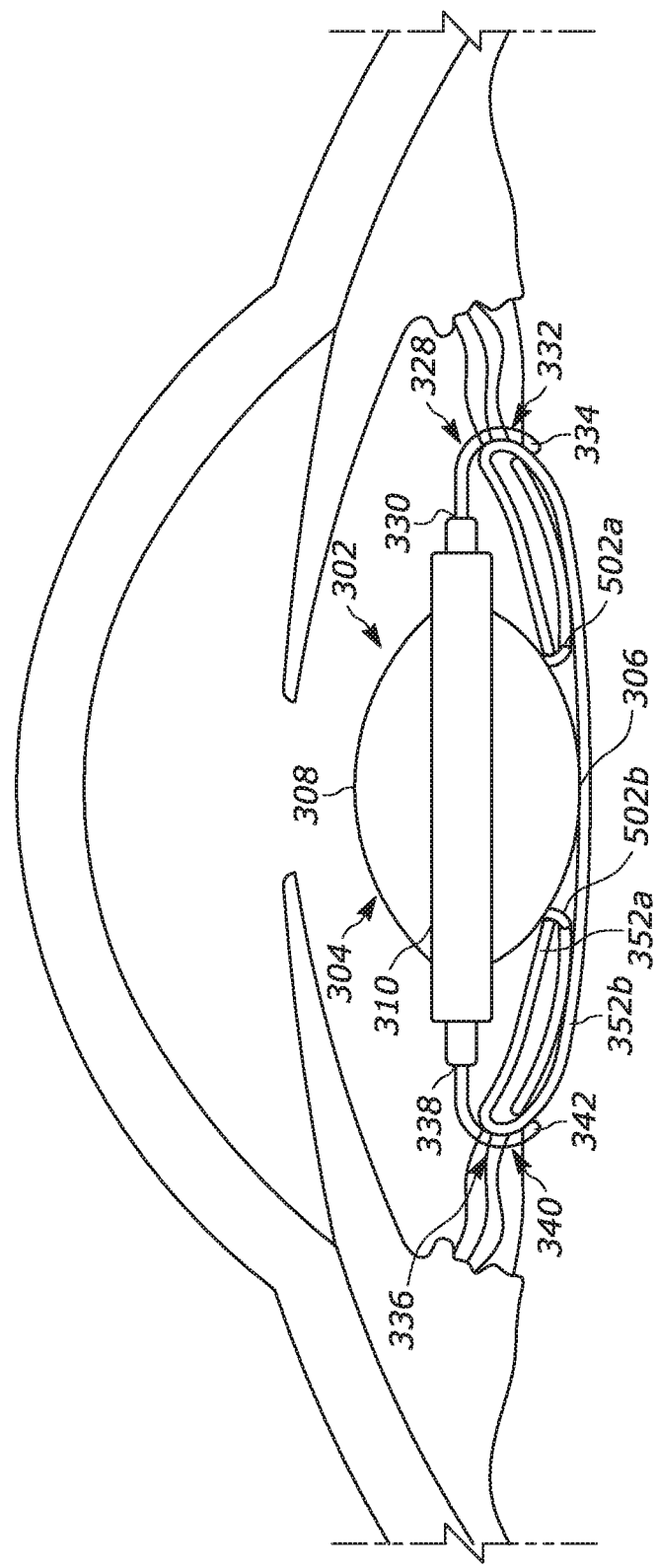
FIG. 29 is a side view of an embodiment of an IOL placed in the patient's eye when the optic of the IOL assumes an accommodated state according to an aspect of the present disclosure.

In an aspect, an IOL can have a compressible membrane disposed circumferentially about a optic. Referring to FIGS. 27 and 28, in an embodiment, IOL 301 can comprise optic 303 having an optical axis extending in an anterior-posterior direction, a posterior face, an anterior face, and an equator extending in a plane substantially perpendicular to the optical axis. Substantially rigid ring 311 can be disposed about the equator of optic 303. Ring 311 is substantially rigid in the sense that when it is pulled, it pulls outward on the optic and does collapse inward. Substantially rigid ring 311 can define interior chamber 315 comprising first portion 317 and second portion 327. First portion 317 can house a first plurality of circumferentially spaced springs 319 connected by first filament 321 having right end 323 and left end 325. Second portion 327 can house a second plurality of circumferentially spaced springs 329 connected by second filament 331 having right end 333 and left end 337. IOL 301 can also include a right connector 339 coupled to substantially rigid ring 311. The right ends 323 and 333 of respective first filament 321 and second filament 331 can be connected to right connector 339. IOL 301 can also include a left connector 342 coupled to relatively rigid ring 311. Left ends 325 and 337 of respective first filament 321 and second filament 331 can be connected to left connector 342. The filaments pass through the ring and are fixed within the haptic such that when the haptics pulls outward, they pulls on the filaments, which flattens the circumferential spaced springs, which, in turn, increases the diameter of the optic and flattens the optic. Although FIGS. 27 and 28 illustrate spring-loaded connectors, such connectors need not be spring loaded. Further, in certain embodiments, the connectors are not present and a membrane is covers the haptics to isolate the moveable parts from eye fluid.

With respect to an exemplary mode of action, with substantially J-shaped haptics, when the ciliary muscle is relaxed and the haptics are pulled outward, the circumferentially spaced springs are pulled taught and the central optic is flattened as illustrated in FIG. 28. When the ciliary muscle contracts the circumferentially spaced springs move inward which allows the optic to round up and the diameter of the optic decreases as illustrated in FIG. 27. This movement may be facilitated by springs coupled to connectors or the haptics or simply by the configuration properties of the optic such that its "relaxed state" is the more rounded position (smaller diameter) and the substantially J-shaped haptics serve to pull the circumferentially spaced springs and result in increasing the diameter of the optic Referring to FIGS. 29-32, in an embodiment, IOL 302 can comprise optic 304 having an optical axis extending in an anterior-posterior direction, posterior face 306, anterior face 308 that can include one or more centration lips 502 to fixate the IOL to the lens capsule, and an equator extending in a plane substantially perpendicular to the optical axis. Substantially rigid ring 310 can be disposed about the equator of optic 304 housing a plurality of circumferentially spaced springs 318. IOL 302 can also includes right connector 322 coupled to the right side of relatively rigid ring 310 and left connector 324 coupled to the left side of substantially rigid ring 310. IOL 302 can also include right haptic 326 having medial portion 328 with medial end 330 and lateral portion 332 with lateral end 334. Medial end 330 of right haptic 326 can be coupled to right connector 322. Likewise, IOL 302 can include left haptic 335 having medial portion 336 with medial end 338 and lateral portion 340 with lateral end 342. Medial end 338 of left haptic 334 can be coupled to left connector 324. Although FIGS. 29-32 illustrate spring-loaded connectors, such connectors need not be spring-loaded. Further, in certain embodiments, the connectors are not present and a membrane is coupled directly to the haptics to isolate the moveable parts from the eye fluid.

The plurality of circumferentially spaced springs 318 can comprise a first set of opposing V-shaped springs 318A and a second set of opposing V-shaped springs 318B. Each opposing V-shaped spring 318 of first set 318A can be connected to opposing walls of the interior chamber 316 at one end and connected to flexible filament 320 at another end. Similarly, each opposing V-shaped spring 318 of second set 318B can be connected to opposing walls of the interior chamber 316 at one end and connected to flexible filament 320 at another end. V-shaped springs 318A and 318B can have a substantially diamond-shape as illustrated in FIGS. 27-28, 30 and 32 such that the springs are connected to each other at one end, and this end is connected to a site of the interior wall. First and second sets 318A and 318B can be equidistantly spaced from one another. The plurality of circumferentially spaced springs 318 can further include equidistantly spaced V-shaped springs 318 between the first and second set of V-shaped springs 318A and 318B.

Figure 32:
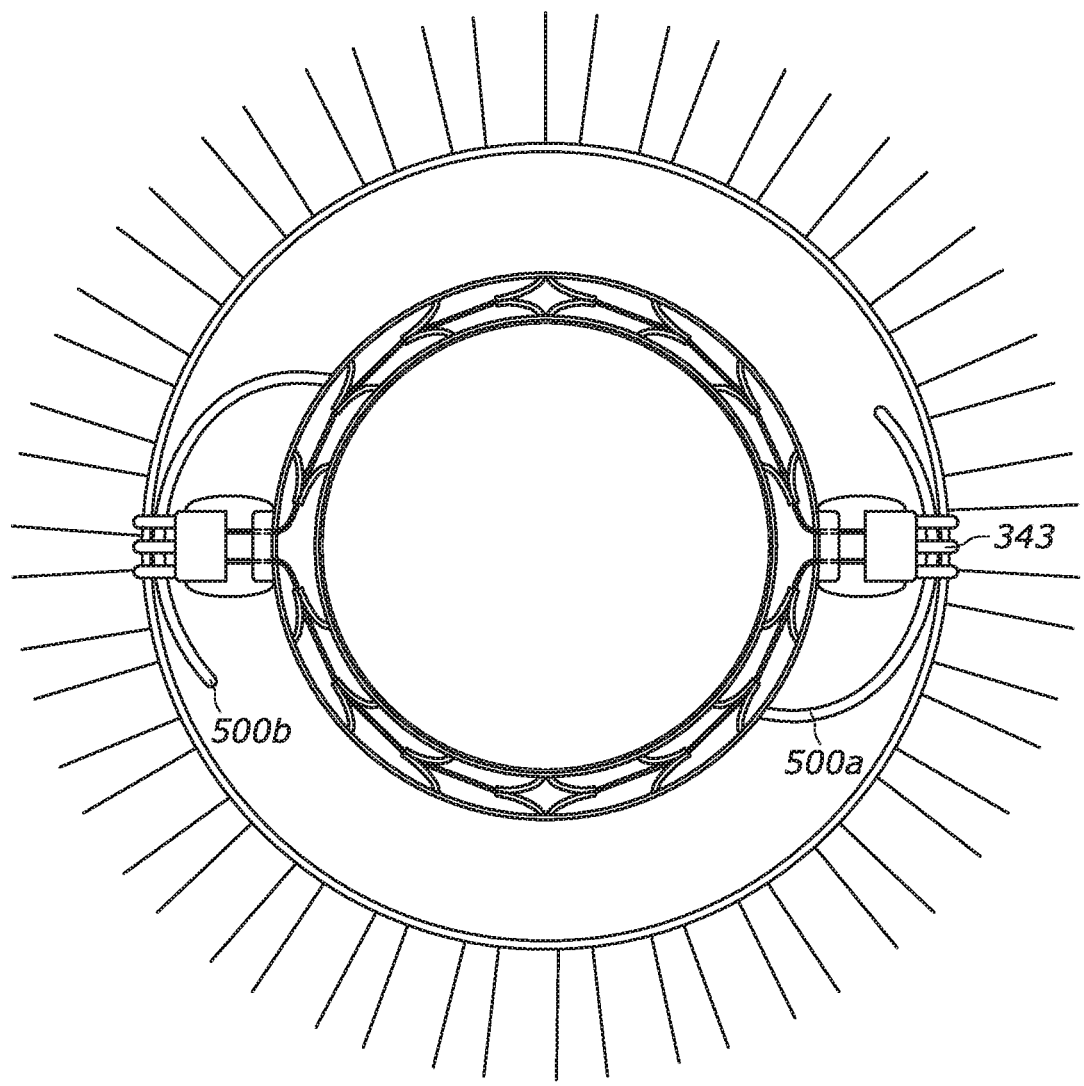
FIG. 32 is a top view an embodiment of the IOL of FIG. 30 including internal components that illustrates the shape of the lens capsule when the optic assumes an un-accommodated state.
Figure 33:
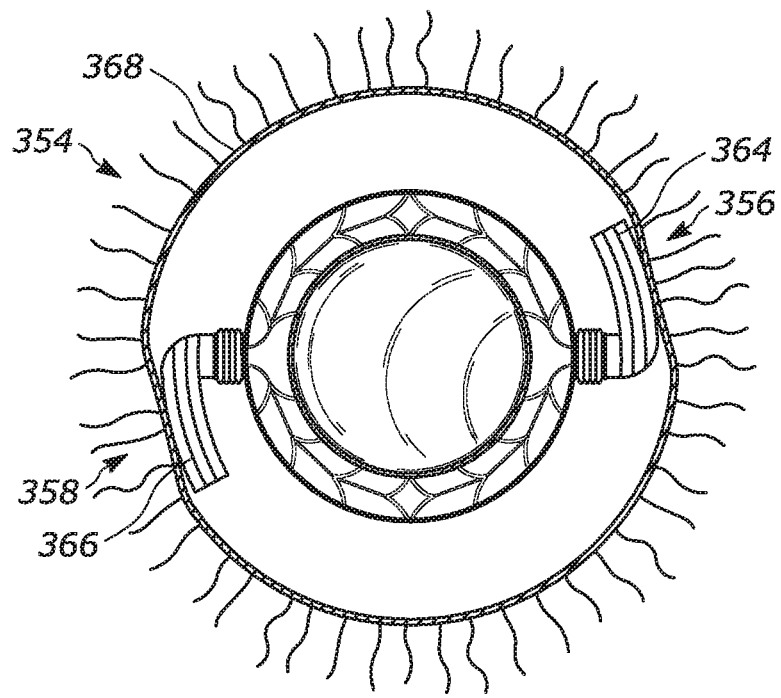
FIG. 33 is a top view of an embodiment of an IOL including internal components that illustrates the shape of the lens capsule when the optic assumes an accommodated state.

With respect to an exemplary mode of action, with substantially J-shaped haptics, when the ciliary muscle is relaxed and the haptics are pulled outward, the circumferentially spaced springs are pulled taught and the central optic is flattened as illustrated in FIG. 32. When the ciliary muscle contracts, the circumferentially spaced springs move inward which allows the optic to round up and the diameter of the optic decreases as illustrated in FIG. 30. This movement may be facilitated by springs coupled to the connectors or haptics, or simply by the configuration properties of the optic such that its "relaxed state" is the more rounded position (smaller diameter) and the substantially J-shaped haptics serve to pull the circumferentially spaced springs and result in increasing the diameter of the optic.

Figure 31:
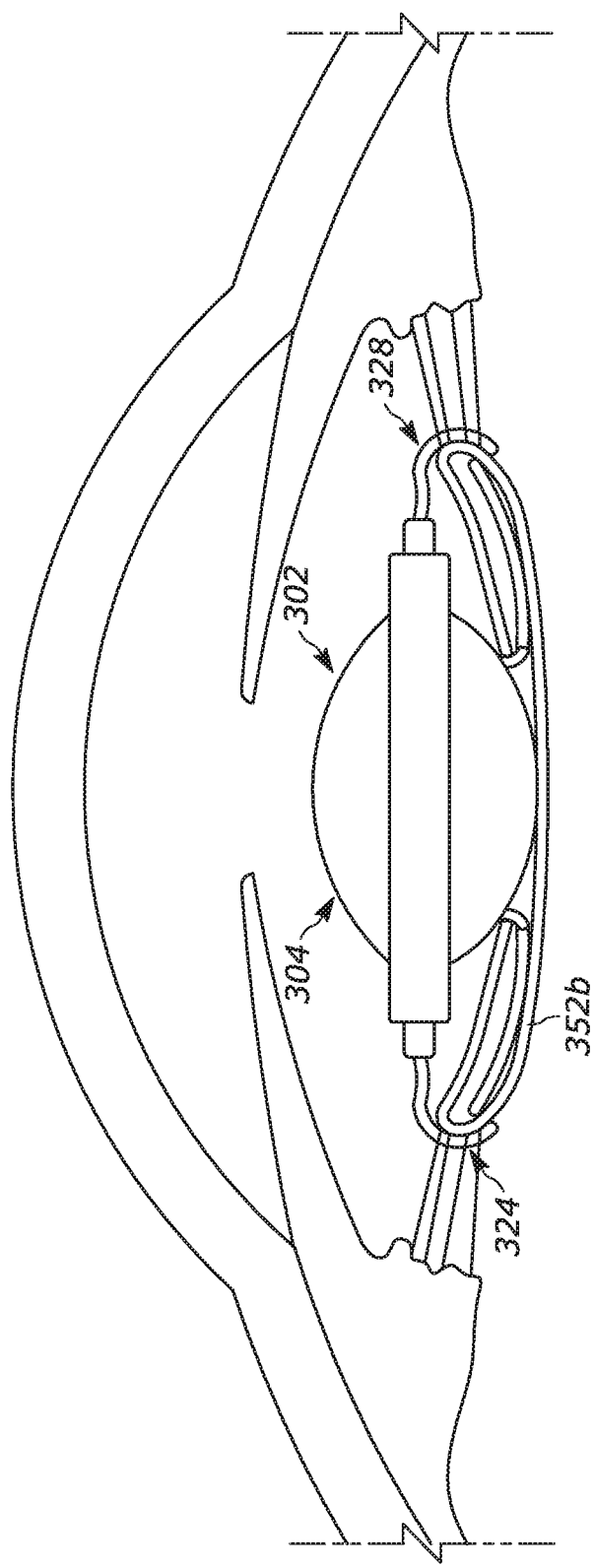
FIG. 31 is a side view of the IOL of FIG. 29 placed in the patient's eye when the optic of the IOL assumes an un-accommodated state according to an aspect of the present disclosure.

The haptics of an IOL as described herein or other IOLs can have a variety of different configurations. As shown in FIG. 29-32, right haptic 326 and left haptic 335 of IOL 302 can each have a hook-shaped/substantially J-shaped configuration. In such a configuration, right haptic 326 and left haptic 335 can each curve around anterior lens capsule 352a to posterior lens capsule 352b. In particular, lateral end 334 of right haptic 326 can curve in a posterior direction towards medial end 330 of right haptic 326 and have an atraumatic tip. Similarly, lateral end 342 of left haptic 335 can curve in a posterior direction towards medial end 338 of left haptic 335 and have an atraumatic tip. Right and left haptics 326 and 335 can each comprise a plurality of hooks, such as at least three hooks 343, as illustrated in FIG. 30. In an accommodated state, lens capsule 352 when placed under tension can result in the areas near the hooks being pulled inward as illustrated in FIG. 32. In un-accommodated state, as illustrated in FIGS. 31 and 32, lens capsule 352 can be pulled flatter and the entire IOL 302 can shift posteriorly. Right and left haptics 326 and 335 can extend in a lateral or posterolateral direction and then extend anteriorly having an anterior curvature around anterior lens capsule. In particular, lateral end 334 of right haptic 326 can extend in a lateral or posterolateral direction, and then can extend in an anterior direction and then can curve in a posterior direction towards medial end 330 of right haptic 326. Similarly, lateral end 342 of left haptic 335 can extend in a lateral or posterolateral direction, then extend in an anterior direction and then can curve in a posterior direction towards medial end 338 of left haptic 335. Lens capsule 352 can have a more uniform shape as the entire lens capsule is under tension in an un-accommodated state as illustrated in FIG. 32. Such a configuration of the haptics can be implemented, for example, when the IOL is fixated in the ciliary sulcus of a patient's eye. Such an embodiment can be implemented in patients that have an already implanted IOL or patients that do not have an already implanted IOL.

As shown in FIGS. 29-32, IOL 302 can include peripheral centering haptics 500 that can extend from fixation members 502 disposed on a posterior surface 306 of optic 304.

Figure 34:
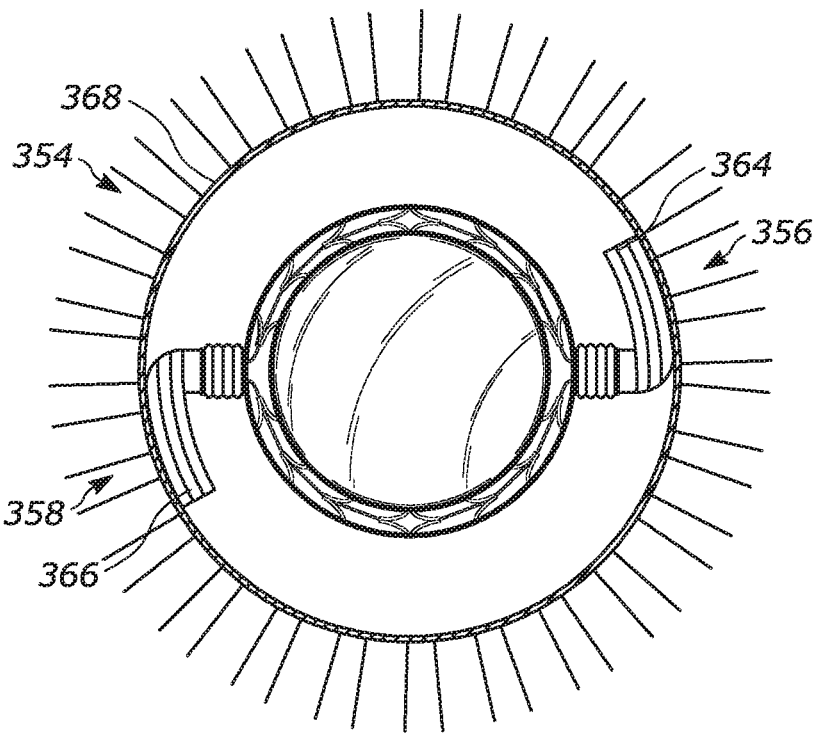
FIG. 34 a top view of the IOL of FIG. 33 that illustrates the shape of the lens capsule when the optic assumes an un-accommodated statek
Figure 35:
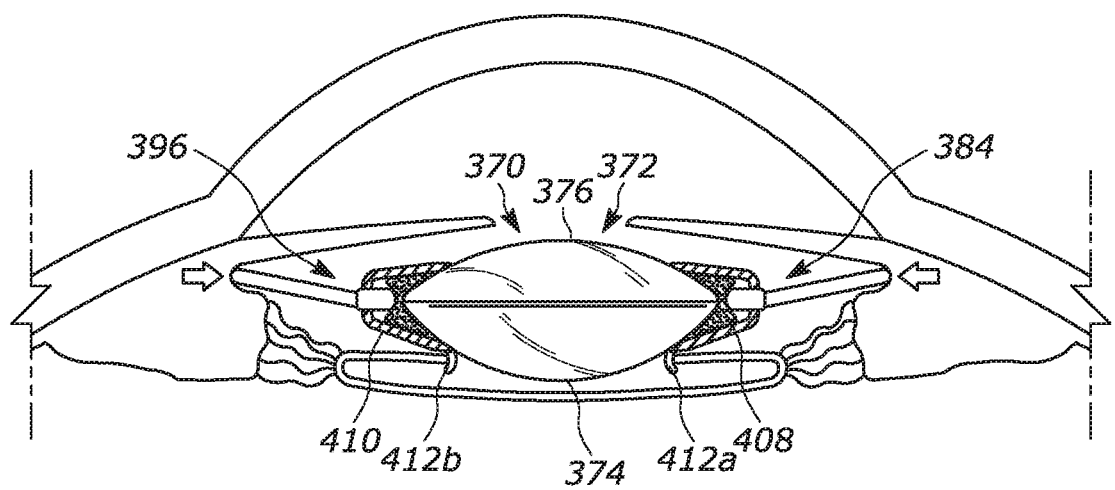
FIG. 35 is a side view of an embodiment of an IOL placed in a patient's eye when the optic of the IOL assumes an accommodated state according to an aspect of the present disclosure.
Figure 36:
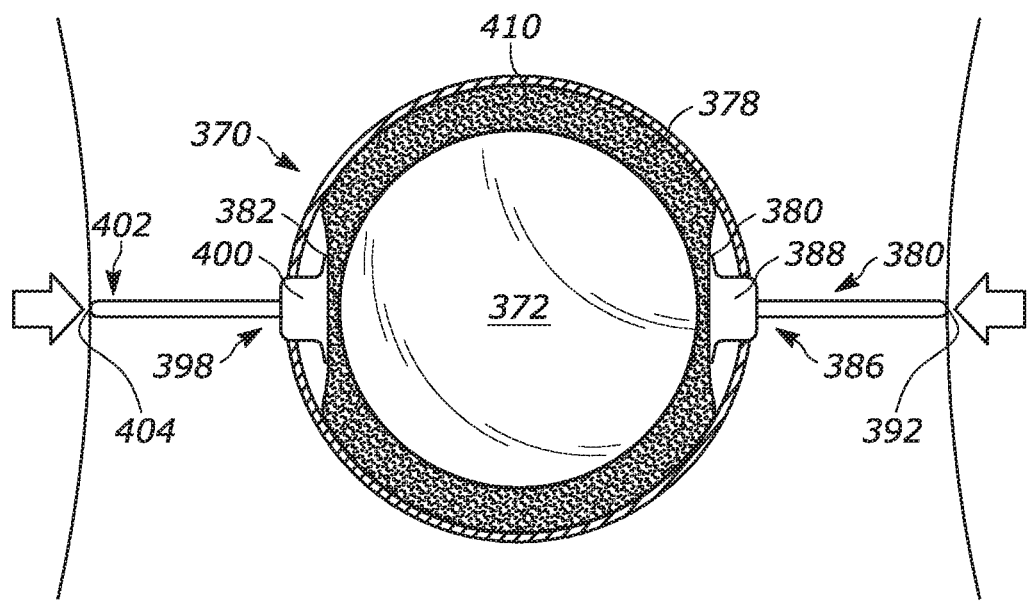
FIG. 36 is a top view of the IOL of FIG. 35 illustrating the internal components of the IOL according to an aspect of the present disclosure.

Referring to FIGS. 34 and 35, which illustrate IOL 354 in an accommodated and un-accommodated state respectively, lateral portions 356 and 358 of respective right haptic and left haptic 360 and 362 can be ridges 364 and 366. Ridges 364 and 366 can interact with the peripheral lens capsule to stabilize the haptics within lens capsule. Similar to the embodiment illustrated in FIGS. 16-17, the leading edges of the lateral portions of the respective right haptic and left haptic can be smooth and narrower than the trailing edges of the lateral ends of the respective right haptic and left haptic. Such a configuration of the haptics can be implemented when the IOL is placed in the lens capsular bag of the patient's eye. In certain embodiments, the portions of the right and left haptics medial to the ridges are plates. The optic can comprises one or more centration lips on an anterior face thereof to keep the optic centered in lens capsule 368.

Figure 37:
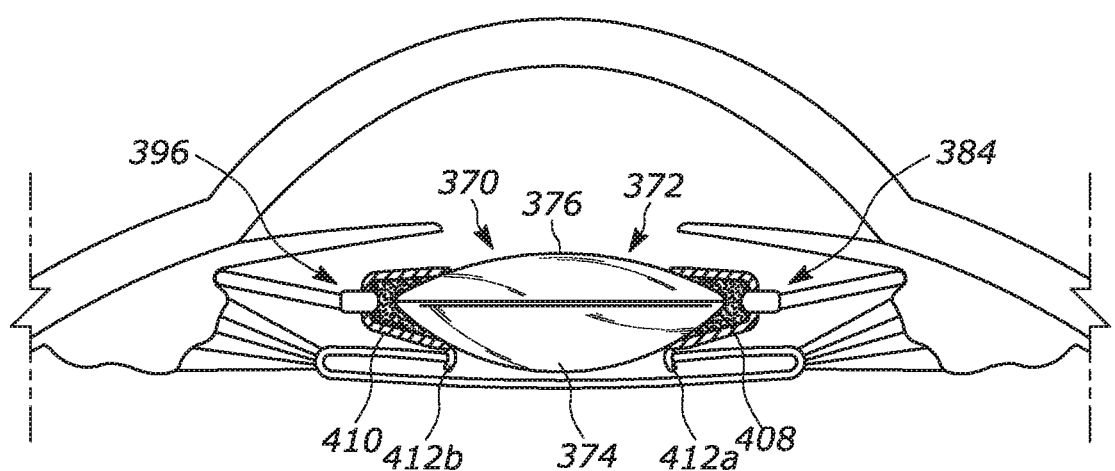
FIG. 37 is a side view of an embodiment of an IOL placed in a patient's eye when the optic of the IOL assumes an un-accommodated state according to an aspect of the present disclosure.
Figure 38:
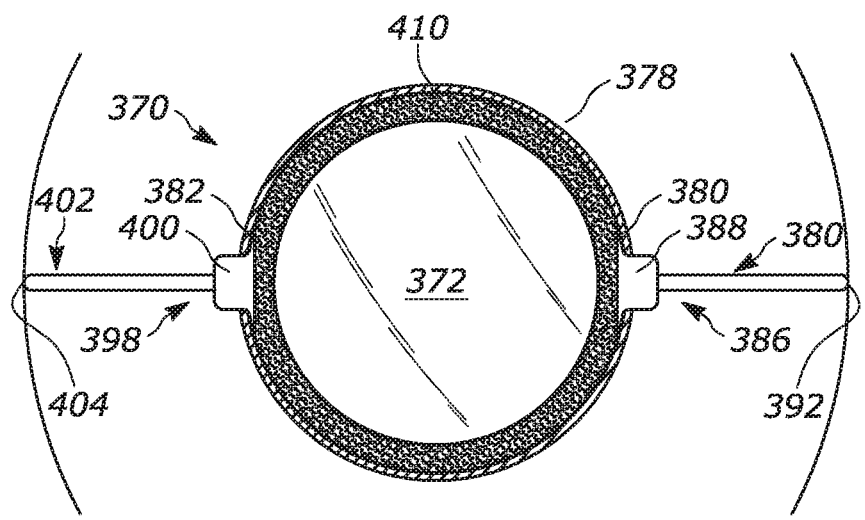
FIG. 38 is a top view of the IOL of FIG. 37 illustrating the internal components of the IOL according to an aspect of the present disclosure.

Referring to FIGS. 37-38, an IOL 370 can include optic 372 having an optical axis extending in an anterior-posterior direction, posterior face 374, anterior face 376, and an equator extending in a plane substantially perpendicular to the optical axis. IOL 370 can further include compressible capsule 378 having right side 380 and left side 382 and disposed about the equator of optic 372. Compressible capsule 378 can comprise interior chamber 408 containing compressible fluid or gel 410. IOL 370 can further include right haptic 384 having medial portion 386 with medial end 388 and lateral portion 390 with lateral end 392. Medial end 388 can be coupled to compressible capsule 378. Likewise, IOL 370 can includes left haptic 396 having a medial portion 398 with a medial end 400 and a lateral portion 402 with a lateral end 404. Medial end 400 can be coupled to compressible capsule 378. As illustrated in FIGS. 36-39, optic 372 can be disposed in optional carrier 410. In such embodiments, one or more centration lips 412 can be disposed on posterior face 414 of the carrier. In embodiments without a carrier, a centration lip can be attached to the optic. The IOL can also have one or more centration lips disposed on an anterior face thereof to center the optic in the lens capsule (in embodiments where the IOL is implanted in the lens capsular bag). A centration lip, can be integral with the anterior and/or posterior face of an optic or integral with the anterior and/or posterior face of a carrier within which an optic rests.

The haptics of an IOL with a compressible capsule can have a variety of different configurations as disclosed herein. Such haptics include, for example, planar or angulated haptics, hook-shaped/substantially J-shaped haptics, haptics with lateral ridges, plate haptics, centration haptics as described herein, as well as other types of haptics to secure the IOL in the ciliary sulcus or the lens capsular bag.

Each of the disclosed aspects and embodiments of the present disclosure may be considered individually or in combination with other aspects and embodiments as well as with respect to other intra-ocular lenses. Further, while certain features of embodiments may be shown in only certain figures, such features can be incorporated into other embodiments shown in other figures or otherwise disclosed in the specification. Additionally, when describing a range, all points within that range are included in this disclosure. In addition, unless otherwise specified, none of the steps of the methods of the present invention are confined to any particular order of performance.

What is claimed is:

1. An accommodating intra-ocular lens (IOL) comprising:
   an optic having an anterior face, a posterior face, a right side, a left side, an optical axis extending in an anterior-posterior direction, an equator extending in a plane substantially perpendicular to the optical axis, an accommodated state, and an un-accommodated state;
   an arcuate sleeve disposed about the equator of the optic and defining a lumen, the sleeve comprising a first sleeve segment and a second sleeve segment;
   an arcuate translating arm disposed about the equator of the optic opposite the sleeve, the translating arm comprising a first translating arm segment glidably received by the first sleeve segment and a second translating arm segment glidably received by the second sleeve segment;
   a first haptic having a lateral portion with a lateral end and a medial portion with a medial end, the lateral end configured to capture an inner or outer periphery of the lens capsule, the medial end coupled to one of the sleeve or the translating arm;

a second haptic having a lateral portion with a lateral end and a medial portion with a medial end, the lateral end of the second haptic configured to capture the inner or outer periphery of a lens capsule, the medial end of the second haptic coupled to the other of the sleeve or the translating arm; and wherein in an accommodated state, the first and second haptics apply linear pressure on the translating arm and/or the sleeve in the plane substantially perpendicular to the optical axis, the linear pressure translating to a substantially circumferential force applied to the optic to reduce an equatorial diameter of the optic.

2. The IOL of claim 1, further comprising one or more centration lips disposed directly or indirectly on the posterior face and/or the anterior face of the optic, the one or more centration lips configured to center the optic in a lens capsulotomy opening.

3. The IOL of claim 2, wherein the one or more centration lips comprises:

a plurality of centration lips equidistantly spaced and disposed directly on the posterior face of the optic to center the optic in a lens capsulotomy opening and to fixate the optic to a lens capsule.

4. The IOL of claim 2, wherein the one or more centration lips comprises:

a plurality of centration lips equidistantly spaced and disposed directly on the anterior face of the optic.

5. The IOL of claim 1, wherein the first haptic and the second haptic each have a substantially J-shaped configuration, the lateral end of the first haptic and the lateral end of the left haptic curving posteriorly towards the medial end of the respective first haptic and the second haptic.

6. The IOL of claim 1, wherein the lateral portions of the first haptic and the second haptic are ridges.

7. The IOL of claim 1, further comprising a compressible capsule having a first side and a second side and disposed about the equator of the optic wherein the medial end of the first haptic is in communication with the first side of the compressible capsule and the medial end of the second haptic is in communication with the second side of the compressible capsule.

* * * * *